(12) United States Patent
Kawabata et al.

(10) Patent No.: US 8,946,357 B2
(45) Date of Patent: *Feb. 3, 2015

(54) ORGANOSILICON COMPOUND, THERMOSETTING RESIN COMPOSITION CONTAINING THE ORGANOSILICON COMPOUND, HARDENING RESIN AND ENCAPSULATION MATERIAL FOR OPTICAL SEMICONDUCTOR

(75) Inventors: Kiichi Kawabata, Kumamoto (JP); Akio Tajima, Kumamoto (JP); Takashi Matsuo, Kumamoto (JP); Kiyoshi Sakai, Kumamoto (JP); Koichi Ayama, Tokyo (JP)

(73) Assignee: JNC Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/698,279

(22) PCT Filed: May 18, 2011

(86) PCT No.: PCT/JP2011/061359
§ 371 (c)(1),
(2), (4) Date: Dec. 17, 2012

(87) PCT Pub. No.: WO2011/145638
PCT Pub. Date: Nov. 24, 2011

(65) Prior Publication Data
US 2013/0096249 A1   Apr. 18, 2013

(30) Foreign Application Priority Data

May 18, 2010 (JP) .................................. 2010-114049

(51) Int. Cl.
*C08F 30/08* (2006.01)
*C09D 183/04* (2006.01)
(Continued)

(52) U.S. Cl.
CPC ............. *C08F 30/08* (2013.01); *C08G 77/045* (2013.01); *C09D 183/04* (2013.01);
(Continued)

(58) Field of Classification Search
CPC .. C09D 183/10; C08G 77/045; C08G 77/485; C08G 77/52; C07F 7/21
USPC ........................................................ 525/478
See application file for complete search history.

(56) References Cited

U.S. PATENT DOCUMENTS 4,510,283 A * 4/1985 Takeda et al. ................. 524/356
6,509,423 B1 * 1/2003 Zhu ............................... 525/478
(Continued)

FOREIGN PATENT DOCUMENTS

JP    61-112334    5/1986
JP    02-289611    11/1990
(Continued)

OTHER PUBLICATIONS

Machine Translation of JP 2007-031619.*
(Continued)

*Primary Examiner* — Mike M Dollinger
(74) *Attorney, Agent, or Firm* — Jianq Chyun IP Office

(57) ABSTRACT

A solution is a liquid organosilicon compound represented by general formula (1) as described below:

(1)

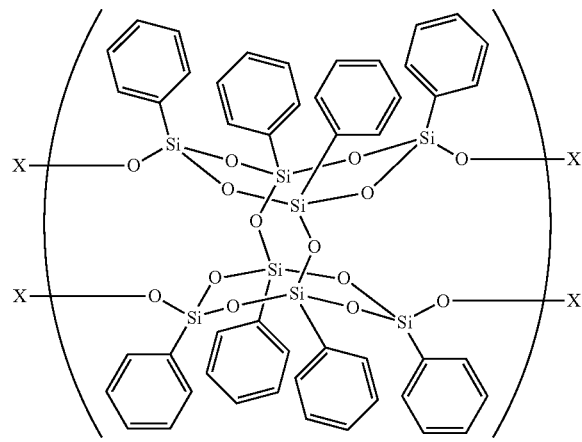

wherein, X is each independently a group represented by formula (I), formula (II) or formula (III) as described below, and when the number of the group represented by formula (I) per one molecule of the liquid organosilicon compound represented by general formula (1) is defined as a, the number of the group represented by formula (II) per one molecule thereof is defined as b, and the number of the group represented by formula (III) per one molecule thereof is defined as c, $0 \leq a \leq 3.5$, $0 \leq b \leq 3.5$, and $0 \leq c \leq 1$ are obtained, and also $a+b+2c=4$ is obtained:

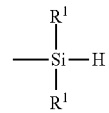

(I)

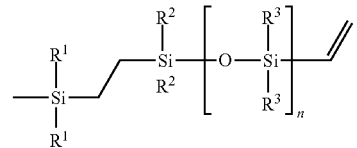

(II)

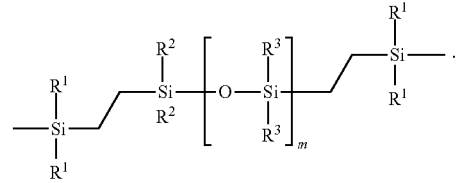

(III)

9 Claims, No Drawings

(51) Int. Cl.
    *C07F 7/21*         (2006.01)
    *C08G 77/04*      (2006.01)
    *H01L 23/29*      (2006.01)
    *C09K 3/10*        (2006.01)
    *C08G 77/20*      (2006.01)
    *C08G 77/00*      (2006.01)
    *H01L 33/56*      (2010.01)

(52) U.S. Cl.
    CPC .............. *H01L 23/296* (2013.01); *C07F 7/21* (2013.01); *C09K 3/1018* (2013.01); *C08G 77/20* (2013.01); *C08G 77/80* (2013.01); *H01L 33/56* (2013.01); *H01L 2924/0002* (2013.01)
    USPC ........................................................ 525/478

(56) References Cited

U.S. PATENT DOCUMENTS

| | | | | |
|---|---|---|---|---|
| 6,689,859 B2* | 2/2004 | Li et al. | ............ | 528/12 |
| 6,774,200 B2* | 8/2004 | Kobayashi et al. | ............. | 528/31 |
| 7,198,639 B2* | 4/2007 | Lai et al. | ...................... | 623/6.11 |
| 7,687,587 B2* | 3/2010 | Smith et al. | .................. | 525/478 |
| 8,273,843 B2* | 9/2012 | Tajima et al. | .................... | 528/31 |
| 2004/0068075 A1* | 4/2004 | Lichtenhan et al. | ............. | 528/15 |
| 2007/0082297 A1* | 4/2007 | Choi et al. | ..................... | 430/311 |
| 2008/0213492 A1* | 9/2008 | Morita | .......................... | 427/387 |
| 2009/0163652 A1* | 6/2009 | Tajima et al. | .................. | 524/612 |
| 2009/0182112 A1* | 7/2009 | Ootake et al. | .................... | 528/33 |
| 2009/0225640 A1* | 9/2009 | Manabe et al. | ................. | 369/100 |
| 2010/0063244 A1* | 3/2010 | Poe et al. | ........................ | 528/332 |
| 2013/0096249 A1* | 4/2013 | Kawabata et al. | ............. | 524/547 |

FOREIGN PATENT DOCUMENTS

| | | |
|---|---|---|
| JP | 2003-277473 | 10/2003 |
| JP | 2004-331647 | 11/2004 |
| JP | 2006-070049 | 3/2006 |
| JP | 2007-045971 | 2/2007 |
| WO | 03/024870 | 3/2003 |
| WO | 2004/024741 | 3/2004 |
| WO | 2004/081084 | 9/2004 |
| WO | 2010/140635 | 12/2010 |

OTHER PUBLICATIONS

Machine Translation of JP 2007-045971.*

* cited by examiner

ORGANOSILICON COMPOUND, THERMOSETTING RESIN COMPOSITION CONTAINING THE ORGANOSILICON COMPOUND, HARDENING RESIN AND ENCAPSULATION MATERIAL FOR OPTICAL SEMICONDUCTOR

CROSS-REFERENCE TO RELATED APPLICATION

This application is a 371 of international application of PCT application serial no. PCT/JP2011/061359, filed on May 18, 2011, which claims the priority benefit of Japan application no. 2010-114049, filed on May 18, 2010. The entirety of each of the above-mentioned patent applications is hereby incorporated by reference herein and made a part of this specification.

TECHNICAL FIELD

The present invention relates to a new organosilicon compound, a thermosetting resin composition that contains the compound and is useful for an application such as an optical material and an electrically insulating material, a hardened material obtained by thermally hardening the composition, and an encapsulation material that uses the hardened material and is for an optical semiconductor.

BACKGROUND ART

A light emitting device such as a light emitting diode (LED) has been put into practical use for various display boards, a light source for reading an image, a traffic light, a unit for a large size display, a backlight of a cellular phone, and so forth in recent years. The light emitting devices are generally encapsulated with a hardening resin obtained by hardening an aromatic epoxy resin with alicyclic acid anhydride being a hardening agent. However, according to the aromatic epoxy resin base, the alicyclic acid anhydride is easily discolored with an acid, or a long period of time is needed until the resin base is hardened, which is known as a problem. Moreover, when the light emitting device is left outdoors or exposed to a light source emitting ultraviolet light, the resin base has a problem of yellowing of the hardening resin used for encapsulation.

In order to solve such a problem, an attempt has been made to apply a method for encapsulating the LED or the like with a hardening resin using an alicyclic epoxy resin or an acrylic resin, and a cationic polymerization initiator (see Patent literature Nos. 1 and 2). However, the hardening resin subjected to cationic polymerization as described above is very brittle and has a disadvantage of easily developing crack destruction by a cold & hot cycle test (also referred to as a heat cycle test). The hardening resin has also a disadvantage of significant coloring of the hardening resin used for encapsulation after hardening thereof, as compared with the hardening resin that has been applied so far in which the aromatic epoxy resin and the acid anhydride are used. Therefore, the hardening resin is unsuitable for an application in which colorless transparency is required, in particular, an application for encapsulating the LED, in which heat resistance and transparency are required.

Consequently, an examination has been made for a resin composition for an LED encapsulation material, in which development of crack destruction by the cold & hot cycle test is improved and light resistance is excellent (see Patent literature No. 3). The resin composition disclosed herein has a hydrogenated epoxy resin or an alicyclic epoxy resin as a matrix component. However, coloring after hardening thereof is still significant. Thus, a further improvement of resistance to discoloration is desired.

Meanwhile, a white LED is increasingly used in an application for lighting or the like, and disregarding of heat generation of an LED package becomes quite difficult with achieving large power thereof. Because yellowing by the heat generation is no longer avoidable when the epoxy resin is used for an encapsulation material, a silicone resin has been used for the encapsulation material of the white LED in place of the epoxy resin. The silicone resin used for the LED is roughly classified into two types, namely, a phenyl silicone resin and a methyl silicone resin.

The phenyl silicone resin generally used has a satisfactory refractive index value, and is superior in heat resistance to the epoxy resin. However, the phenyl silicone resin is not enough to respond to achieving high power of LED. While the methyl silicone resin is superior in heat resistance and light resistance, the refractive index is low. Therefore, light extraction efficiency of the LED is poor.

Therefore, an encapsulation material that can respond to achieving high power of the white LED, and has both a high refractive index and a good heat resistance to satisfy close contact also, and a thermosetting resin composition used therefor have been required.

Moreover, as compared with the epoxy resin, a hardened material using the silicone resin such as the methyl silicone resin and the phenyl silicone resin has a poorer close contact with a polyamide resin used for an LED substrate and silver used for an electrode, and has had a disadvantage of easily causing peeling by a heat shock or the like.

The methyl silicone resin and the phenyl silicone resin mainly have a polysilsesquioxane compound having a branched structure by a hydrolytic condensation reaction of an alkoxysilane monomer, as a main structure. However, the resins each have a residual silanol group, and therefore have had a problem of causing a change in physical properties, such as a temporal change in hardness by the heat shock or the like. For example, when exposed to high temperature conditions as in a reflow process, the resins have had a disadvantage of easily causing cracks by a hardness rise.

On the other hand, Patent literatures Nos. 4 to 8 disclose a cage-type silicon compound and a polymer thereof, and describe to the effect that heat resistance is satisfactory. The compound and the polymer include a cage-type silsesquioxane in which a structure is controlled, as commonly referred to as a double decker, which is different from a structure of polysilsesquioxane having a random structure ordinarily obtained from the hydrolytic condensation reaction of alkoxysilane. Furthermore, the compound and the polymer do not have a silanol group having a defect in storage stability or causing a hardness rise due to secondary hardening after thermal hardening. Therefore, the compound and the polymer are considered to be suitable for an application such as an LED-use encapsulation material in which long-term reliability is required. However, the compound and the polymer each are solid or crystal, and require a solvent for molding for practical use purpose. Thus, the compound and the polymer as are have been quite difficult to respond to the LED or the like.

Moreover, Patent literature No. 9 discloses an encapsulant-use composition containing a cage-type silicon compound, and an encapsulant. Patent literature 9 discloses a hardened material prepared by obtaining a thermosetting polymer by a hydrosilylation reaction between a cage-type silicon compound having a SiH group and a compound having a vinyl group, and further allowing hardening by hydrosilylation with a compound having a vinyl group. However, the description in Patent literature No. 9 is unclear, and also the hardened material is quite difficult to obtain by the method described in the Patent literature.

CITATION LIST

Patent Literature

Patent literature No. 1: JP S61-112334 A.
Patent literature No. 2: JP H02-289611 A.
Patent literature No. 3: JP 2003-277473 A.
Patent literature No. 4: JP 2006-070049 A.
Patent literature No. 5: WO 2004/081084 A.
Patent literature No. 6: JP 2004-331647 A.
Patent literature No. 7: WO 2003/24870 A.
Patent literature No. 8: WO 2004/24741 A.
Patent literature No. 9: JP 2007-45971 A.

SUMMARY OF INVENTION

Technical Problem

One of objectives of the invention is to provide a silicone resin-based thermosetting resin composition that can yield a hardened material having a high refractive index and a good heat resistance. Another objective of the invention is to provide a silicone resin-based thermosetting resin having improved close contact with a thermoplastic resin such as a polyamide resin used for an LED substrate, and a metal such as silver used for an electrode. A further objective of the invention is to provide a silicone resin-based thermosetting resin having resistance to causing a change in physical properties due to a hardness rise, and an excellent crack resistance. A still further objective of the invention is to provide a hardening composition containing the thermosetting resin composition to allow wide provision of a composition having viscosity from an optimum viscosity range from 1 Pa·s to 10 Pa·s suitable for a dispenser system being an LED-use encapsulation method to a high viscosity range of 10 Pa·s or more suitable for a mold system. A still further objective of the invention is to provide a new organosilicon compound to be contained in the thermosetting resin composition, a hardened material composed of a thermosetting silicone resin composition, a molded object, and an optical encapsulation material for a light emitting diode or the like.

Solution to Problem

The present inventors have diligently continued to conduct research for achieving the objectives as described above. As a result, the present inventors have succeeded in synthesis of a new liquid organosilicon compound including a cage-type silicon compound structure. The present inventors have found that the organosilicon compound needs no solvent because the compound is liquid, a hardened material obtained from a thermosetting resin composition containing the organosilicon compound and a hardening agent is excellent inclose contact with a polyamide resin and silver, and also excellent in a refractive index, transparency, heat resistance, resistance to thermal yellowing, or the like, and has a small change in physical properties due to a hardness rise, and is excellent in crack resistance, and thus have completed the invention.

More specifically, the invention has a constitution as described below.

Item 1. A liquid organosilicon compound represented by formula (1) as described below:

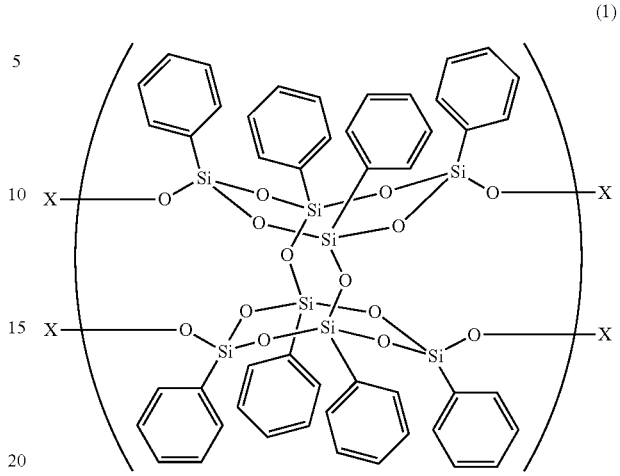

(1)

wherein, X is each independently a group represented by formula (I), formula (II) or formula (III) as described below, and when the number of the group represented by formula (I) per one molecule of the liquid organosilicon compound represented by the general formula (1) (or the number of groups per one mean molecule of the compound when the compound is a mixture having a different ratio for the group represented by formula (I), the group represented by formula (II) and the group represented by formula (III)) is defined as a, the number of the group represented by formula (II) per one molecule thereof is defined as b, and the number of the group represented by formula (III) per one molecule thereof is defined as c, 0≤a 3.5, 0≤b≤3.5, and 0≤c≤1 are obtained, and also a+b+2c=4 is obtained:

(I)

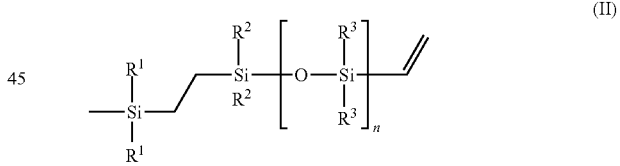

(II)

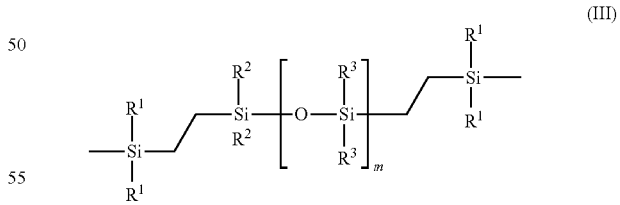

(III)

wherein, $R^1$ is each independently a group selected from alkyl having 1 to 4 carbons, cyclopentyl and cyclohexyl, $R^2$ and $R^3$ are each independently a group selected from alkyl having 1 to 4 carbons, cyclopentyl, cyclohexyl and phenyl, m and n are the number of repetitions of —$OSi(R^3)_2$—, and a mean value satisfying 1 to 50.

Item 2. A method for manufacturing the liquid organosilicon compound according to item 1, including a process for allowing a hydrosilylation reaction between a compound represented by general formula (2-1) as describe below and a compound represented by general formula (2-2) as described below, wherein (a) based on the number of moles of the compound represented by the general formula (2-1), (b) the compound represented by the general formula (2-2) is added in an amount of twice or more the number of moles to allow reaction and liquefaction:

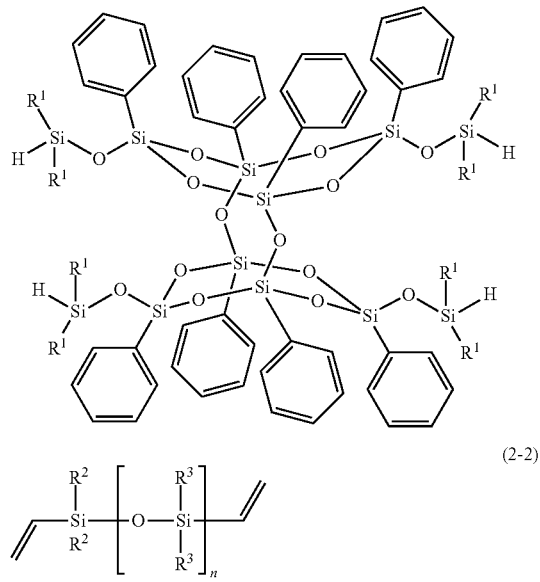

(2-1)

(2-2)

wherein, in the general formulas (2-1) and (2-2), $R^1$, $R^2$, $R^3$ and n are defined in a manner similar to the definitions in general formula (1).

Item 3. A thermosetting resin composition containing the liquid organosilicon compound according to item 1.

Item 4. The thermosetting resin composition according to item 3, further containing a liquid organosilicon compound obtained from a constitutional unit represented by C, and a constitutional unit represented by D in formula (3):

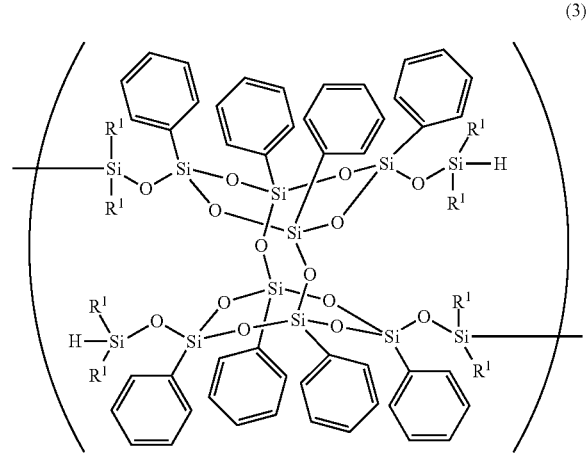

(3)

Constitutional unit C

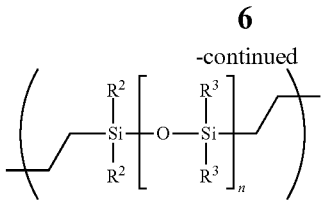

Constitutional unit D wherein, in the formula (3), $R^1$ is each independently a group selected from alkyl having 1 to 4 carbons, cyclopentyl and cyclohexyl, $R^2$ and $R^3$ are each independently a group selected from alkyl having 1 to 4 carbons, cyclopentyl, cyclohexyl and phenyl, n is the number of repetitions of —$OSi(R^3)_2$—, and a mean value satisfying 2 to 50, and when a molar fraction of the constitutional unit represented by C in the liquid organosilicon compound is defined as a, and a molar fraction of the constitutional unit represented by D in the liquid organosilicon compound is defined as β, a ratio of α to (n×β), (α:(n×β), satisfies 1:3 to 1:100.

Item 5. The thermosetting resin composition according to item 3 or 4, further containing a platinum catalyst.

Item 6. The thermosetting resin composition according to any one of items 3 to 5, further allowing dispersion of silica and/or a phosphor.

Item 7. A hardened material, formed by thermally hardening the thermosetting resin composition according to any one of items 3 to 6.

Item 8. A molded object obtained by molding the hardened material according to item 7.

Item 9. A coating film, formed by applying the thermosetting resin composition according to any one of items 3 to 6.

Item 10. An encapsulation material for an optical semiconductor, composed of the thermosetting resin composition according to any one of items 3 to 6.

Advantageous Effects of Invention

A hardened material of a thermosetting resin composition of the invention is excellent in a high refractive index, transparency, heat resistance, resistance to thermal yellowing, or the like. Therefore, a molded object formed of the hardened material can be suitably used for an application such as an encapsulation material for a semiconductor, an encapsulation material for an optical semiconductor, a die bonding material for the optical semiconductor, an insulating film, a sealing agent, an optical lens, or the like. The molded object can also be used for a transparent material, an optical material, an optical film, an optical sheet, an adhesive, an electronic material, an insulating material, an interlayer insulating film, paint, ink, a coating material, a molding material, a potting material, a liquid crystal sealing agent, a sealing agent for a display device, an encapsulation material for a solar battery, a resist material, a color filter, a material for electronic paper, a material for a hologram, a material for the solar battery, a material for a fuel battery, a display material, a recording material, a waterproof material, a damp-proof material, a solid electrolyte for a battery, and a gas separation film. The hardened material can also be used for an additive to any other resin, or the like.

DESCRIPTION OF EMBODIMENTS

<Organosilicon Compound of the Invention>

An organosilicon compound of the invention is represented by general formula (1) as described below.

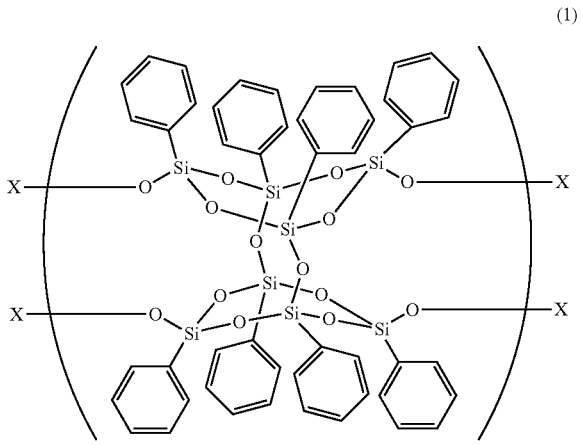

(1)

In the formula (1), X is each independently a group represented by formula (I), formula (II) or formula (III) as described below, and when the number of the group represented by the general formula (I) per one molecule of a liquid organosilicon compound represented by the general formula (1) (or the number of groups per one mean molecule of the compound when the compound is a mixture having a different ratio for the group represented by formula (I), the group represented by formula (II), and the group represented by formula (III)) is defined as a, the number of the group represented by formula (II) per one molecule thereof is defined as b, and the number of the group represented by formula (III) per one molecule thereof is defined as c, $0 \leq a \leq 3.5$, $0 \leq b \leq 3.5$, and $0 \leq c \leq 1$ are obtained, and also $a+b+2c=4$ is obtained:

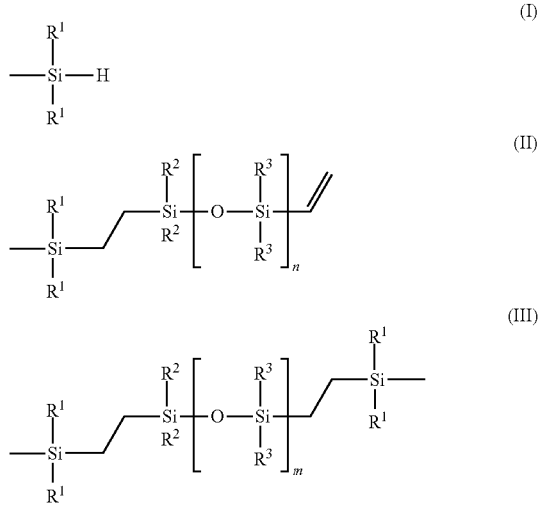

wherein, $R^1$ is each independently a group selected from alkyl having 1 to 4 carbons, cyclopentyl and cyclohexyl, $R^2$ and $R^3$ are each independently a group selected from alkyl having 1 to 4 carbons, cyclopentyl, cyclohexyl and phenyl, m and n are the number of repetitions of $—OSi(R^3)_2—$, and a mean value satisfying 1 to 50.

Then, a and b as described above are also the number of a SiH group and the number of a vinyl group, respectively, per one molecule of the liquid organosilicon compound represented by the general formula (1) (or the number of groups per one mean molecule when the compound is a mixture of compounds having a different ratio for the group represented by formula (I) and the group represented by formula (II)). If a is 0 to 3.5 ((b+2c) is 0.5 to 4.0), the liquid organosilicon compound can be yielded. When a is larger than 3.5 ((b+2c) is smaller than 0.5), a large amount of solid of the formula (2-1) that is not involved in a reaction is contained therein is not fully dissolved to be deposited, and thus the liquid compound is not formed. Moreover, c is the number of a component for crosslinking molecules of the liquid organosilicon compound represented by the general formula (1) with each other. More specifically, the component contains neither the SiH group nor the vinyl group, and therefore is not involved in a ratio of the SiH group or the vinyl group. Moreover, an amount of the solid of the formula (2-1) can be relatively reduced by increasing the present component, and therefore the liquid organosilicon compound can be easily yielded.

In the invention, the organosilicon compound in the range satisfying $a+b+2c=4$, $0 \leq a$, $b \leq 3.5$, and $0 \leq c \leq 1$ will be explained.

If a>b, the organosilicon compound represented by the general formula (1) according to the invention includes, on average, a larger number of the SiH group than the number of the vinyl group, and can be defined as a so-called SiH group-type thermosetting resin, and if a<b, the organosilicon compound represented by the general formula (1) according to the invention can be defined as a so-called vinyl group-type polymer. Moreover, if a=b, the organosilicon compound represented by the general formula (1) according to the invention can be defined as a thermosetting resin having an equal number of the SiH group and the vinyl group.

When the SiH group-type thermosetting resin is yielded, a as described above is preferably 1.0 to 3.0, further preferably, 1.5 to 2.5 from a viewpoint of remarkably exhibiting excellent characteristics upon yielding the hardened material.

When the vinyl group-type thermosetting resin is yielded, the resin can be used in a wide range such that the resin can also be combined with the organosilicon compound of the invention in which a>b as described above is satisfied, and can be hardened in combination with the liquid organosilicon compound represented by formula (3) as described later.

Moreover, as a value of c becomes larger, the component for crosslinking the molecules with each other further increases to yield a compound having a larger molecular weight. If c=0, the compound is in a state of no presence of the crosslinking component. Therefore, if a and b are in the range described above, a compound having a comparatively low viscosity is yielded. In a range of $0<c \leq 1$, as a value of c becomes larger, the crosslinking component further increases, and the viscosity of the compound becomes higher. Furthermore, in a range of c>1, the compound is in a state in which crosslinking of the molecules with each other significantly progresses, and becomes gelled, and is quite difficult to keep a liquid state. The viscosity of the compound can be adjusted by changing the value of c within the range of $0 \leq c \leq 1$.

The organosilicon compound of the invention is obtained, for example, by allowing a hydrosilylation reaction between a silsesquioxane derivative represented by general formula (2-1) as described below and diorganopolysiloxane having vinyl groups at both ends as represented by general formula (2-2) as described below with a reaction molar ratio of 2 or more.

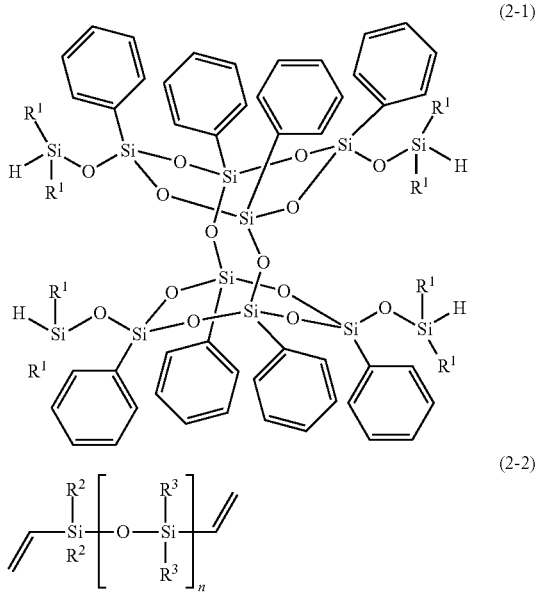

(2-1)

(2-2)

In the formula (2-1), $R^1$ is each independently a group selected from alkyl having 1 to 4 carbons, cyclopentyl and cyclohexyl. In formula (2-2), $R^2$ and $R^3$ are each independently a group selected from alkyl having 1 to 4 carbons, cyclopentyl, cyclohexyl and phenyl. $R^1$, $R^2$ and $R^3$ are preferably methyl, ethyl or propyl, further preferably, methyl. Then, n is the number of repetitions of —OSi $(R^3)_2$—, and a mean value satisfying 1 to 50.

In the organosilicon compound represented by formula (1) according to the invention, in order to yield the liquid compound, a structure is controlled by suppressing a crosslinking reaction. Specifically, a reaction is allowed in an amount of twice or more the number of moles of the general formula (2-2) based on the number of the moles of the general formula (2-1). More specifically, only one end of the diorganopolysiloxane compound having the vinyl groups at ends as represented by the general formula (2-2) is selectively introduced partially or wholly into four SiH groups in the general formula (2-1), and thus an organosilicon compound having a desired ratio of SiH group: vinyl group can be yielded. Thus, although the compound of the general formula (2-1) is solid, a flexible polysiloxane chain having a high degree of freedom is bonded with the compound of the general formula (2-1), and thus the liquid organosilicon compound can be yielded. If the reaction molar ratio is in the range of 1 or more to less than 2, the crosslinking reaction easily occurs, more specifically, the hydrosilylation reaction between produced monomers progresses, leading to a highly viscous liquid or even gelation to yield no liquid. Moreover, a suitable amount of diorganopolysiloxane having the vinyl groups at ends as represented by general formula (2-2) can be allowed to react before the reaction described above. The crosslinking reaction of the compound of the general formula (2-1) progresses by the reaction, and an amount of the solid of the general formula (2-1) in the compound can be reduced. An amount of the compound of the general formula (2-2) is 1 or less based on 1 mole of the compound of the general formula (2-1).

A publicly known method can be applied to the hydrosilylation reaction between the compound (2-1) and the compound (2-2), and the reaction can be performed in a solvent or in absence of solvent. The solvent used for the hydrosilylation reaction is not particularly limited, if the solvent does not adversely affect the progress of the reaction. A preferred solvent include a hydrocarbon solvent such as hexane and heptane, an aromatic hydrocarbon solvent such as benzene, toluene and xylene, an ether solvent such as diethyl ether, tetrahydrofuran (THF) and dioxane, a halogenated hydrocarbon solvent such as methylene chloride and carbon tetrachloride, and an ester solvent such as ethyl acetate. The solvents may be used alone or in combination of a plurality thereof. Among the solvents, the aromatic hydrocarbon solvent is particularly preferred, and among the aromatic hydrocarbon solvents, toluene is most preferred.

The hydrosilylation reaction can be performed at room temperature (25° C.) and under ordinary pressure (1 bar), but heating is preferred in order to promote the reaction. When the reaction is performed in absence of solvent, the reaction between the compound (2-1) and the compound (2-2) both being raw materials is necessarily performed in a homogeneous system, and therefore preferably performed in a temperature range from 100° C. to 150° C. When no reaction solvent is used, the reaction may be performed at a temperature equal to or higher than a temperature in which all raw materials yield the homogeneous system. However, as described later, an amount of hydrosilylation catalyst to be used in the invention is limited. Thus, the reaction is performed under heating at a temperature of 80° C. or higher, preferably, 100° C. or higher, further preferably, in the range of 110° C. to 150° C. The hydrosilylation reaction can be more easily promoted by adding the hydrosilylation catalyst. Examples of a preferred hydrosilylation catalyst include a Karstedt catalyst, a Speier catalyst and a hexachloroplatinic acid. The catalysts are generally well known.

Next, an amount of the hydrosilylation catalyst to be added will be explained. Because reactivity of the hydrosilylation catalysts is high, the reaction can be sufficiently promoted by addition of a small amount of the catalysts. However, a preferred catalyst concentration range is different depending on the organosilicon compounds that satisfy the range of a, b and c. A value of a decreases as hydrosilylation during the reaction progresses. More specifically, when the value of a is desirably decreased, furthermore specifically, when the reaction is desirably sufficiently promoted, the catalyst concentration may be increased. On the contrary, when the value of a is desirably increased, further more preferably, when the reaction is not desired to be sufficiently promoted, the catalyst concentration may be decreased.

When a Pt catalyst is used for the organosilicon compound of the invention, an amount of Pt is preferably in the concentration range of 0.001 to 0.08 ppm based on the compound represented by formula (2-1). When the concentration range is described in more detail, the concentration range of 0.001 ppm to 0.04 ppm is further preferred in the range of $1.5 \le a \le 3.5$, and the concentration range of 0.04 ppm to 0.1 ppm is preferred in the range of $0.8 \le a \le 1.5$. If the concentration range is in the ranges described above, the organosilicon compound of the invention can be easily controlled in the reaction and without thickening in an after-treatment process, and also has a good storage stability at ordinary temperature. If the concentration range is deviated from the ranges, a period of time needed for the reaction to reach a desired value of a may become very long, or the reaction may abruptly progress to be difficult in controlling the reaction, and thickening in the after-treatment process and also a decrease in storage stability at ordinary temperature may be caused.

When a is smaller than 0.8, reactivity between the vinyl group and the SiH group is low. Therefore, an amount of Pt is preferably in the range of 0.1 ppm to 5 ppm based on the compound represented by formula (2-1).

A method for removing the solvent used in the reaction, or unreacted vinyl silicone being an unreacted raw material compound will be explained. The unreacted vinyl silicone referred to herein means an unreacted portion that has not contributed to the reaction among excess amounts of the diorganopolysiloxane having the vinyl groups at both ends as used during the hydrosilylation reaction. Volatile vinyl silicone can be removed by distillation. Moreover, vinyl silicone having a high boiling point or non-volatility can be removed by a solvent extraction method utilizing a difference in solvent partition. Moreover, vinyl silicone has two or more functional groups, and therefore may be arbitrarily left as is, or may be used as the thermosetting resin composition.

When vinyl silicone having a low boiling point is removed by distillation, attention is needed so as to avoid progress of the hydrosilylation reaction during distillation because the organosilicon compound satisfying $0.8 \leq a \leq 3.5$ according the invention has both the SiH group and the vinyl group. In a distillation method in which a heat history cannot be avoided as in a simple distillation operation, distillation is desirably performed at a temperature equal to or lower than a reaction temperature. A temperature during removal of an excess amount of vinyl silicone in the simple distillation operation is preferably 60 to 100° C., further preferably, 70° C. to 90° C. If a temperature exceeds the preferred ranges, the hydrosilylation reaction progresses during distillation, and a compound having a desired ratio of the vinyl group and the SiH group may no longer be obtained. Moreover, a hardening retarder for delaying the progress of the hydrosilylation reaction may be arbitrarily added in distillation so as to avoid the progress of the hydrosilylation reaction during distillation. Furthermore, a distillation method by means of a thin-film evaporator may also be applied in order to avoid the heat history. As for a distillation temperature in the above case, the distillation may be performed at a distillation temperature equal to or higher than the reaction temperature because of no fear of progress of the hydrosilylation reaction by the heat history. In particular, when high-boiling point diorganopolysiloxane having the vinyl groups at both ends is used for the reaction, and an excess portion thereof is desirably removed, thin film distillation is preferably applied. An upper limit of the temperature is not particularly provided, but the range of 120° C. to 180° C. is preferred.

Moreover, removal of low-volatile vinyl silicone can be achieved by a solvent washing method utilizing a difference in solvent partition. A preferred solvent for dissolving vinyl silicone has a large dissolving power and a relatively low boiling point. A preferred washing solvent is lower alcohol. A particularly preferred washing solvent is methanol. In order to further increase a degree of purification, times of repetitions of a solvent extraction operation may be increased.

The organosilicon compound of the invention is characterized by being liquid. The organosilicon compound and the polymer thereof that have been known so far are in a solid state or a crystal state, and have needed to be dissolved in a solvent for allowing easy molding, thereby forming a coating film by application, and then pouring the coating film into a mold to yield a molded object. However, the organosilicon compound of the invention does not need to be dissolved in a solvent, is obviously easily molded, and in a liquid state having a good fluidity even at room temperature, and therefore excellent in handling properties. Moreover, upon yielding the compound as the thermosetting resin composition, the hardened material is excellent in transparency, heat resistance, and also close contact and so forth.

Moreover, as for the organosilicon compound of the invention, the hardened material obtained by preparing the composition containing the composition and hardening the composition is excellent in close contact with the polyamide resin and silver, and also in a refractive index, transparency, heat resistance, resistance to thermal yellowing and so forth. Therefore, the organosilicon compound of the invention is an excellent raw material for the hardened material in which a disadvantage of the hardened material composed of silicone resin such as a phenyl silicone resin and a methyl silicone resin that has been applied so far is improved. When the composition is used for hardening for the LED or the like, if the refractive index of the hardened material is 1.4 or more, the compound can be utilized without any problem. The refractive index is preferably 1.50 or more, and an upper limit is not particularly limited.

In addition, the silsesquioxane derivative represented by the general formula (2-1) can be prepared by the method disclosed in WO 2004/024741 A, for example. An example of the compound represented by the general formula (2-1) (hereinafter, expressed as "DD-4H") is shown below.

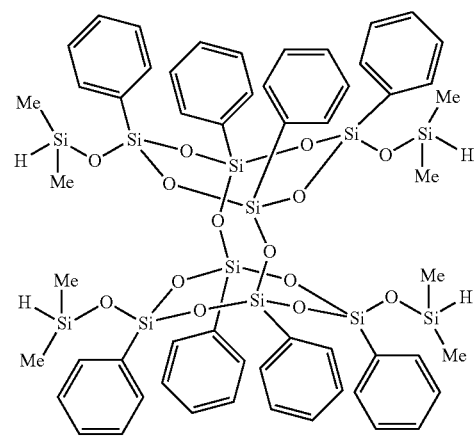

Moreover, the diorganopolysiloxane having the vinyl groups at both ends as represented by the general formula (2-2) can be prepared by a publicly known method, or a commercially available compound may also be used. The compound represented by the general formula (2-2) can be manufactured using 1, 5-divinylhexamethyltrisiloxane (hereinafter, expressed as "DVTS") represented by a structure as described below, for example. In addition thereto, specific examples include 1,3-divinyl-1,3-dimethyl-1,3-diphenyldisiloxane. Moreover, a value of n in the general formula is 1 to 50, preferably, 2 to 30, further preferably, 2 to 20. The value of n in the general formula can be adjusted by suitably selecting a molar ratio of raw materials (1,3-divinyltetramethyldisiloxane and octamethylcyclotetrasiloxane, for example) upon synthesis.

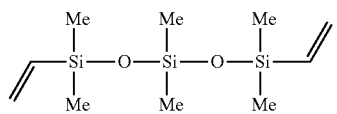

The thermosetting resin composition of the invention contains the liquid organosilicon compound represented by the general formula (1), or the liquid organosilicon compound obtained by allowing the hydrosilylation reaction between the compound represented by the general formula (2-1) and the compound represented by the general formula (2-2). A hardening catalyst is added to the thermosetting resin composition, and the resultant mixture was heated, and thus the hardened material is yielded.

In the organosilicon compound of the invention, if a>b, the compound is the SiH group-type thermosetting resin. Therefore, a preferred embodiment includes a case where the thermosetting resin composition further contains a silicon compound having two or more vinyl groups, such as diorganopolysiloxane. The silicon compound having two or more vinyl groups is not particularly limited, if the silicon compound has two or more vinyl groups for crosslinking. For example, straight-chain polysiloxane having vinyl groups at both ends can be used. Specific examples include straight-chain polysiloxane having vinyl groups at both ends, such as DVTS. The silicon compound having two or more vinyl groups may be used in one kind or by blending two or more different kinds of compounds. In the thermosetting resin composition of the invention, a content ratio of the SiH group in total and the vinyl group in total is preferably 1:2 to 2:1 in terms of a functional group molar ratio of the SiH group to the vinyl group.

In the organosilicon compound of the invention, if the range is a<b, the compound is the vinyl group-type thermosetting resin. Therefore, in the above case, a preferred embodiment also includes a case where the thermosetting resin composition of the invention further contains an organosilicon compound having a SiH group represented by general formula (3) as described below. The compound is a polymer composed of constitutional unit C and constitutional unit D, and a preferred range of molecular weight is 3,000 to 100,000 in weight average molecular weight.

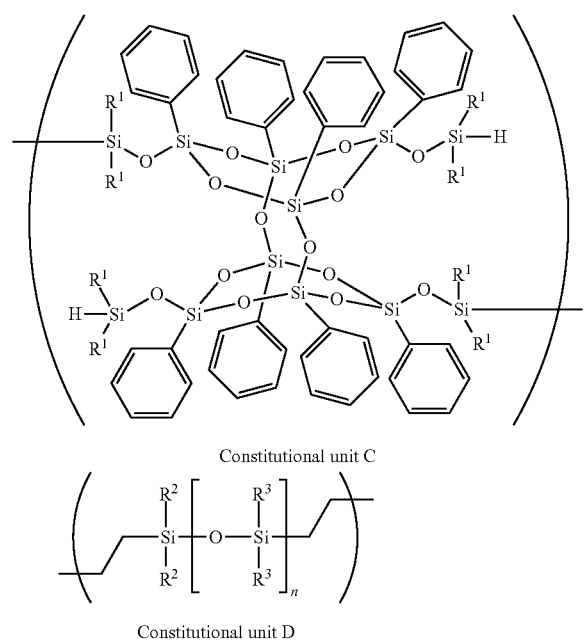

Constitutional unit C

Constitutional unit D (3)

In the general formula (3), $R^1$ is each independently a group selected from alkyl having 1 to 4 carbons, cyclopentyl and cyclohexyl, $R^2$ and $R^3$ are each independently a group selected from alkyl having 1 to 4 carbons, cyclopentyl, cyclohexyl and phenyl. $R^1$, $R^2$ and $R^3$ are preferably methyl, ethyl or propyl, further preferably, methyl. Then, n is the number of repetitions of —$OSi(R^3)_2$—, and a mean value satisfying 2 to 50.

When a molar fraction of the constitutional unit represented by C in the liquid organosilicon compound is defined as α, and a molar fraction of the constitutional unit represented by D in the liquid organosilicon compound is defined as β, a ratio of a to (n×β), (α:(n×β)), satisfies 1:3 to 1:100.

The compound is obtained by performing the hydrosilylation reaction at a reaction molar ratio of 0.75 for the diorganopolysiloxane having the vinyl groups at both ends as represented by the general formula (2-2) based on the silsesquioxane derivative represented by the general formula (2-1). In the thermosetting resin composition of the invention, a content ratio of the SiH group in total and the vinyl group in total is preferably 1:2 to 2:1 in terms of a functional group molar ratio of the SiH group to the vinyl group.

The hardening catalyst is not particularly limited, if the catalyst is a transition metal catalyst ordinarily used as a reaction catalyst, but a platinum catalyst is preferably used. As an example of the platinum catalyst, an ordinary hydroxylation catalyst can be selected. Specific examples of a preferred hydrosilylation catalyst include a Karstedt catalyst, a Speier catalyst and a hexachloroplatinic acid. The catalysts are a generally well-known platinum catalyst.

An amount of the catalyst to be used is 0.1 ppm to 10 ppm in terms of a weight ratio of a transition metal contained in the catalyst based on the thermosetting resin composition. If an addition ratio is in the range described above, the composition hardly causes defective hardening, has no fear of causing a disadvantage of incapability of use due to too short pot life after preparing the thermosetting resin composition, and also causes no coloring of the hardened material. A preferred addition ratio is 0.5 ppm to 4 ppm.

The thermosetting resin composition of the invention can be utilized even without using any solvent. As already described, polysilsesquioxane is solid, but the organosilicon compound represented by the general formula (1) according to the invention is liquid. More specifically, the composition of the invention is also liquid. Therefore, the composition can be used in an application in which mixing of a solvent is not preferred, and an application range is significantly expanded.

A component as described below may be further compounded with the thermosetting resin composition of the invention.

(i) Powdery reinforcing agent or filler, for example, a metal oxide such as aluminum oxide and magnesium oxide, a silicon compound such as micronized silica, fused silica and crystalline silica, a transparent filler such as glass beads, a metal hydroxide such as aluminum hydroxide, and also kaolin, mica, quartz powder, graphite and molybdenum disulfide. The components are compounded in the range in which transparency of the thermosetting resin composition of the invention is not adversely affected. A preferred ratio in compounding the components is in the range of 0.1 to 0.9 in terms of a weight ratio based on the total amount of the thermosetting resin composition of the invention.

(ii) Coloring agent or a pigment, for example, titanium dioxide, molybdenum red, Prussian blue, ultramarine, cadmium yellow, cadmium red and an organic dye.

(iii) Flame retarder, for example, antimony trioxide, a bromine compound and a phosphorus compound.

(iv) Ion adsorbent.

A preferred ratio in compounding the components from (ii) to (iv) is 0.0001 to 0.30 in terms of a weight ratio based on the total amount of the thermosetting resin composition.

(v) Silane coupling agent.

(vi) Nanoparticle dispersion liquid of a metal oxide such as zirconia, titania, alumina and silica.

A preferred ratio in compounding the components from (v) to (vi) is 0.01 to 0.50 in terms of a weight ratio based on the total amount of the thermosetting resin composition.

(vii) Antioxidant such as a phenol-based, sulfur-based or phosphorus-based antioxidant. A preferred ratio in using antioxidant is in the range of 0.0001 to 0.1 in terms of a weight ratio based on the total amount of the thermosetting resin composition.

(viii) Ultraviolet absorber for improving light resistance. A preferred ratio in using the ultraviolet absorber is in the range of 0.0001 to 0.1 in terms of a weight ratio based on the total amount of the thermosetting resin composition.

The thermosetting resin composition of the invention can be prepared by the method described below, for example. The organosilicon compound of the invention, the hardening catalyst, and when necessary, an arbitrary component as described above are mixed, and the resultant mixture is subjected to agitation, and then vacuuming and deformation. Then, the resultant mixture is poured into a mold, and subjected to heating at 80° C. for 1 hour, and finally heating at 150° C. for 1 to 5 hours, and thus the mixture can be hardened.

As for transparency of the hardened material, when a transmittance of the hardened material before and after a heat-resistance test is measured by means of a UV-Vis spectrophotometer and a retention rate of a luminous transmittance at 400 nm is evaluated, the retention rate of a luminous transmittance at 180° C. is preferably 90% or more. When each value enters within the above ranges, the hardened material shows to be colorless and highly transparent, and can be particularly preferably utilized in a field such as an encapsulant for an optical semiconductor in which transparency is required.

Excellent characteristics of heat-resistant transparency of the hardened material formed by thermally hardening the thermosetting resin composition of the invention are attributed to the structure of the silsesquioxane derivative represented by the general formula (2-1). More specifically, absence of a silanol group in a skeleton of double-decker silsesquioxane gives excellent properties to heat-resistant transparency, and simultaneously suppresses a physical change, for example, a rise of hardness over time by heating.

The hardened material formed by thermally hardening the thermosetting resin composition of the invention is molded to yield the molded object, and thus the molded object can be used in various applications. Silica or a phosphor is dispersed into the composition, and thus the composition has a light-emitting function and can be used as an LED composition. Moreover, specific examples of the applications include an optical semiconductor encapsulation material, a semiconductor encapsulation material, a die bonding material for the optical semiconductor, an insulating film, a sealing material, an adhesive and an optical lens.

EXAMPLES

The invention will be explained in more detail based on Examples. In addition, the invention is not limited by Examples described below.
<Measurement of Number Average Molecular Weight and Weight Average Molecular Weight>

Number average molecular weight and weight average molecular weight of a polymer prepared according to the invention were measured as described below.

High-performance liquid chromatograph system CO-2065plus made by Jasco Corporation was used. As an analytical sample, 20 μL of THF solution having a sample concentration of 1% by weight was used. Measurement was carried out according to a GPC method using a column: Shodex KF804L (made by Showa Denko K. K.) (two columns connected in series), a column temperature: 40° C., a detector: RI, and an eluate: THF, and at an eluate flow rate: 1.0 mL per minute, and the average molecular weight was determined by calculating a polystyrene equivalent.
<Nuclear Magnetic Resonance Spectrum (NMR)>

Then, 400 MHZ NMR (made by JEOL Datum Ltd.) was used. A measurement sample was dissolved in deuterated chloroform, and then the NMR spectrum was measured.
<Viscosity>

Viscosity was measured by using a cone plate type TV-22 viscometer (made by Toki Sangyo Co., Ltd.) at a temperature of 25° C. in a constant temperature bath.

Reagents and so forth used in Examples are as described below: 1,3-divinyltetramethyldisiloxane (DVDS): made by GELEST, Inc.; 1,5-divinylhexamethyltrisiloxane (DVTS): made by GELEST, Inc.; and diphenyldimethoxysilane: made by GELEST, Inc.

Synthesis Example 1

Synthesis of Silsesquioxane Derivative (DD-4H)

Into a reaction vessel equipped with a reflux condenser, a thermometer and a dropping funnel, 6.54 kg of phenyltrimethoxysilane, 0.88 kg of sodium hydroxide, 0.66 kg of water and 26.3 L of 2-propanol were charged. Heating was started under a nitrogen gas flow while agitating the resultant mixture. After continuing agitation for 6 hours from starting reflux, the resultant mixture was allowed to stand overnight at room temperature. Then, the resultant reaction mixture was transferred to a filter, and filtered by pressurizing the mixture with a nitrogen gas. A solid obtained was washed once with 2-propyl alcohol, and filtration was performed, and then the resultant cake was dried at 80° C. under reduced pressure, and thus 3.3 kg of colorless solid (DD-ONa) represented by a formula as described below was obtained.

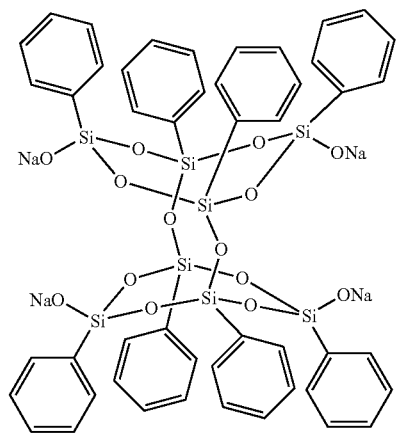

Next, into a reaction vessel equipped with a reflux condenser, a thermometer and a dropping funnel, 2,005 g of cyclopentyl methyl ether, 243 g of 2-propanol, 1,400 g of ion exchange water and 461 g of hydrochloric acid were charged, and the resultant mixture was agitated at room temperature under a nitrogen atmosphere. Subsequently, 800 g of the compound (DD-ONa) obtained and 2,003 g of cyclopentyl methyl ether were charged into the dropping funnel to be formed in a slurry state, and the resultant slurry was added dropwise to the reaction vessel over 30 minutes, and agitation was continued for 30 minutes after completion of dropwise addition. After the reaction, agitation was stopped and the resultant mixture was allowed to stand, and separated into an organic layer and an aqueous layer. The resultant organic layer was washed with water and adjusted to be neutral, and then dust was removed with a membrane filter, and the resultant mixture was concentrated at 60° C. under reduced pressure using a rotary evaporator, and thus 678 g of colorless solid was obtained. The colorless solid was washed with 980 g of methyl acetate and dried under reduced pressure, and thus 496 g of powdery colorless solid (DD-4OH) represented by a formula as described below was obtained.

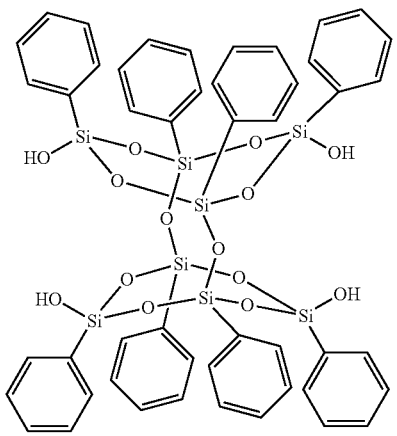 [SMILES: O[Si]1(c2ccccc2)O[Si]2(c3ccccc3)O[Si](O)(c3ccccc3)O[Si](c3ccccc3)(O1)O[Si]1(c3ccccc3)O[Si](O)(c3ccccc3)O[Si](c3ccccc3)(O[Si](O)(c3ccccc3)O1)O2]

Next, into a reaction vessel equipped with a dropping funnel, a thermometer and a reflux condenser, 7,160 g of the compound (DD-4OH) obtained, 72,600 g of toluene and 2,850 g of dimethylchlorosilane were charged, and sealing was performed with dry nitrogen. Subsequently, 3,230 g of triethylamine was added dropwise from the dropping funnel for about 20 minutes. Herein, a rate of dropwise addition was adjusted to be 35° C. to 40° C. in a solution temperature. After completion of dropwise addition, agitation was continued for 1 hour to complete a reaction. After completion of the reaction, 16,700 g of ion exchange water was poured into the vessel to hydrolyze an excess amount of dimethylchlorosilane, and the resultant mixture was separated into an organic layer and an aqueous layer. The organic layer was washed with water and adjusted to be neutral, concentrated at 85° C. under reduced pressure using a rotary evaporator. A residue obtained was washed with 19, 950 g of methanol, and thus 8,587.6 g of colorless solid was obtained. The colorless solid was washed with 9,310 g of methyl acetate, dried under reduced pressure, and thus 7,339 g of powdery colorless solid was obtained. The colorless solid obtained is judged to have a structure (DD-4H) as described below from analytical results as described below.

$^1$H-NMR (solvent: CDCl$_3$): δ (ppm); 0.16 (d, 24H), 4.84-4.89 (m, 4H), 7.05-7.50 (m, 40H). $^{29}$Si-NMR (solvent: CDCl$_3$): δ (ppm); 3.85 (s, 4Si), −71.90 (s, 4Si), −75.05 (s, 4Si).

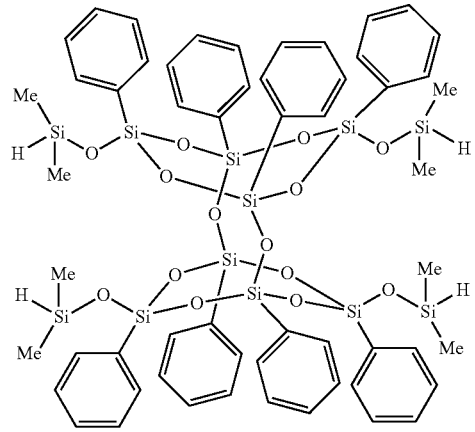 [SMILES: C[SiH](C)O[Si]1(c2ccccc2)O[Si]2(c3ccccc3)O[Si](O[SiH](C)C)(c3ccccc3)O[Si](c3ccccc3)(O1)O[Si]1(c3ccccc3)O[Si](O[SiH](C)C)(c3ccccc3)O[Si](c3ccccc3)(O[Si](O[SiH](C)C)(c3ccccc3)O1)O2]

Synthesis Examples 2 to 5

Synthesis of Diorganopolysiloxane 1 to Diorganopolysiloxane 4

Synthesis Example 2

To a 1,000 mL 4-necked flask, magnetic stirrer, a cooling tube and a thermometer were attached, and 400 g (2.15 mol) of 1,1,3,3-divinyltetramethyldisiloxane, 212 g (0.716 mol) of octamethylcyclotetrasiloxane and 4.5 g (1 wt. %) of activated clay as an acid catalyst were charged thereinto. After increasing temperature to 80° C. and allowing reaction for 22 hours, the resultant mixture was cooled to room temperature and the activated clay was removed by filtration using 5C filter paper. A filtrate was transferred to a recovery flask, a low boiling point portion was distilled off under conditions of 80° C. and a reduced pressure of 5 mmHg by means of an evaporator, and thus 314 g of colorless transparent liquid (diorganopolysiloxane 1) was obtained. Measurement of Si—NMR was carried out, and from a ratio of integrated intensity of a peak of Si at an end of a molecular chain and a peak of Si inside the molecular chain, n (mean value) in a formula as described below was calculated to be 3.9, and a vinyl group equivalent to be 188 g/mol.

Synthesis Examples 3 to 5

Diorganopolysiloxane 2 to diorganopolysiloxane 4 were prepared in a manner similar to Synthesis Example 2 except for an amount of charging 1,3-divinyltetramethyldisiloxane (DVDS) and octamethylcyclotetrasiloxane (D4), and also conditions for distilling the low boiling point portion.

Table 1 shows n (mean value) and the vinyl equivalent for diorganopolysiloxane 1 to diorganopolysiloxane 4.

TABLE 1

| | Diorgano-polysiloxane | DVDS (g) | D4 (g) | Cutting conditions | Yield (g) | Vinyl group equivalent (g/mol) | n (Mean value) |
|---|---|---|---|---|---|---|---|
| Synthesis Example 1 | 1 | 400 | 212 | 80° C., 5 mmHg | 314 | 188 | 3.9 |
| Synthesis Example 2 | 2 | 350 | 279 | 80° C., 5 mmHg | 450 | 227 | 5 |
| Synthesis Example 3 | 3 | 150 | 239 | 90° C., 1 mmHg | 222 | 360 | 8.5 |
| Synthesis Example 4 | 4 | 100 | 250 | 70° C., 1 mmHg | 300 | 450 | 12 |

Synthesis Example 6

Synthesis of Diorganopolysiloxane Having a Phenyl Group Partially in a Side Chain To a 300 mL 4-necked flask, a magnetic stirrer, a cooling tube and a thermometer were attached, and 14.9 g (0.08 mol) of 1,3-divinyltetramethyldisiloxane, 89 g (0.3 mol) of octamethylcyclotetrasiloxane, 97.7 g (0.4 mol) of diphenyldimethoxysilane and 0.1 g of KOH ground with a mortar as an alkali catalyst were charged thereinto. Thereto, 7.2 g (0.4 mol) of pure water was added, and the resultant mixture was heated to 120° C. A reaction was allowed for 24 hours while draining methanol and water generated in hydrolysis. The resultant mixture was cooled to room temperature, neutralized with formic acid, and then repeatedly washed with pure water. A liquid after washing with water was transferred to a recovery flask. A low boiling point portion was distilled off under conditions of 120° C. and a reduced pressure of 1 mmHg by means of an evaporator, and thus 132 g of colorless transparent liquid (diorganopolysiloxane Ph) was obtained. Measurement of Si—NMR was carried out, and from a ratio of integrated intensity of a peak of Si at an end of a molecular chain and a peak of Si inside the molecular chain, a product is represented by a reaction formula as described below. In the formula described below, n (mean value) was calculated to be 14+5=19, and a vinyl group equivalent to be 1,900 g/mol.

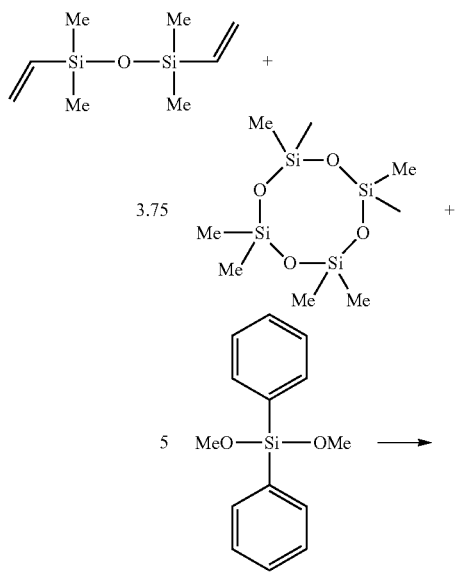

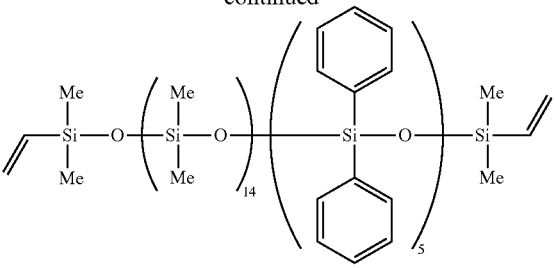

Synthesis Example 7

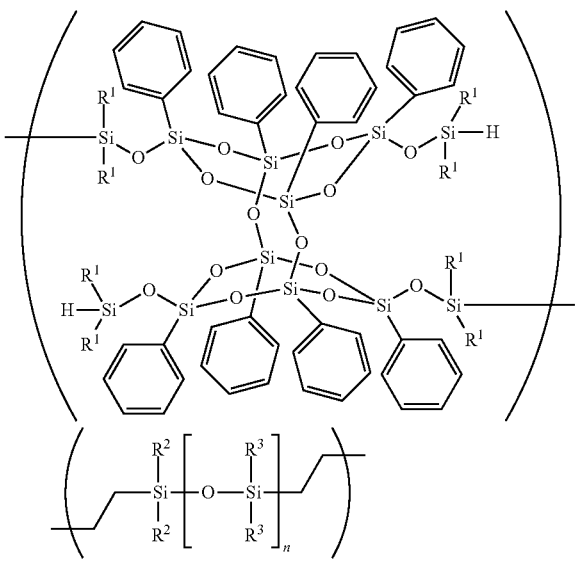

(3)

To a 2,000 mL 4-necked flask, magnetic stirrer, a cooling tube and a thermometer were attached, and 100 g of silsesquioxane derivative (DD-4H) manufactured in Synthesis Example 1, 57.8 g (0.75-fold moles based on the mole of DD-4H) of diorganopolysiloxane 2 having vinyl groups at both ends as manufactured in Synthesis Example 3 and 890 g of toluene as a solvent were charged thereinto.

Heating agitation was started under a nitrogen atmosphere. After the contents reached 70° C., a Karstedt catalyst was added to be 0.1 ppm based on DD-4H, and a reaction was performed at 70° C. for 3 hours, and thereafter at 100° C. for 3 hours. Then, disappearance of a vinyl group peak (5.9 to 6.3 ppm) was confirmed by H-NMR, and the reaction was completed. A reaction mixture obtained was transferred to a recovery flask, and toluene was distilled off under conditions of 100° C. and a reduced pressure of 5 mmHg by means of an evaporator.

A viscous liquid obtained was dissolved in 350 g of acetone, 1.7 g of activated carbon was added, and the resultant mixture was agitated for 5 hours. The activated carbon was filtered off under reduced pressure using a 0.2 μL filter. A filtrate was put in the evaporator again, and acetone was distilled off under conditions of 70° C. and a reduced pressure of 5 mmHg by means of the evaporator, and thus 157 g of colorless viscous liquid was obtained.

Analysis of molecular weight by means of GPC yielded number average molecular weight: Mn=2,200 and weight average molecular weight: Mw=6,800. Moreover, a SiH equivalent was 850 g/mol.

Example 1

Compound (1-1) was manufactured by a reaction as described below.

moles based on the mole of DD-4H) of DVTS and 37.5 g of toluene as a solvent were put. Heating agitation was started under a nitrogen atmosphere. After the contents reached 115° C., a Karstedt catalyst was added to be 0.004 ppm in a Pt concentration based on DD-4H, and heating agitation was continued. The reaction was tracked by GPC, and the reaction was terminated by stopping heating after 7 hours. A reaction mixture was transferred to a recovery flask, and toluene and an excess portion of DVTS were distilled off under conditions of 70° C. and a reduced pressure of 1 mmHg by means of an evaporator, and thus 58 g of colorless transparent liquid having a viscosity (at 25° C.) of 95 Pa·s was obtained. Analysis of molecular weight by means of GPC yielded number average molecular weight: Mn=1,200 and weight average molecular weight: Mw=1,400. The colorless transparent liquid obtained is judged to have a structure as described below from analytical results as described below.

$^1$H-NMR (solvent: CDCl$_3$): δ (ppm); 0.0-0.6 (m, 50.8H), 5.0 (s, 2.4H), 5.8-6.4 (m, 3.2H), 7.05-7.50 (m, 40H).

Then, a=2.4 was obtained, a SiH equivalent was 670 g/mol and a vinyl group equivalent was 1,500 g/mol.

(1-1)

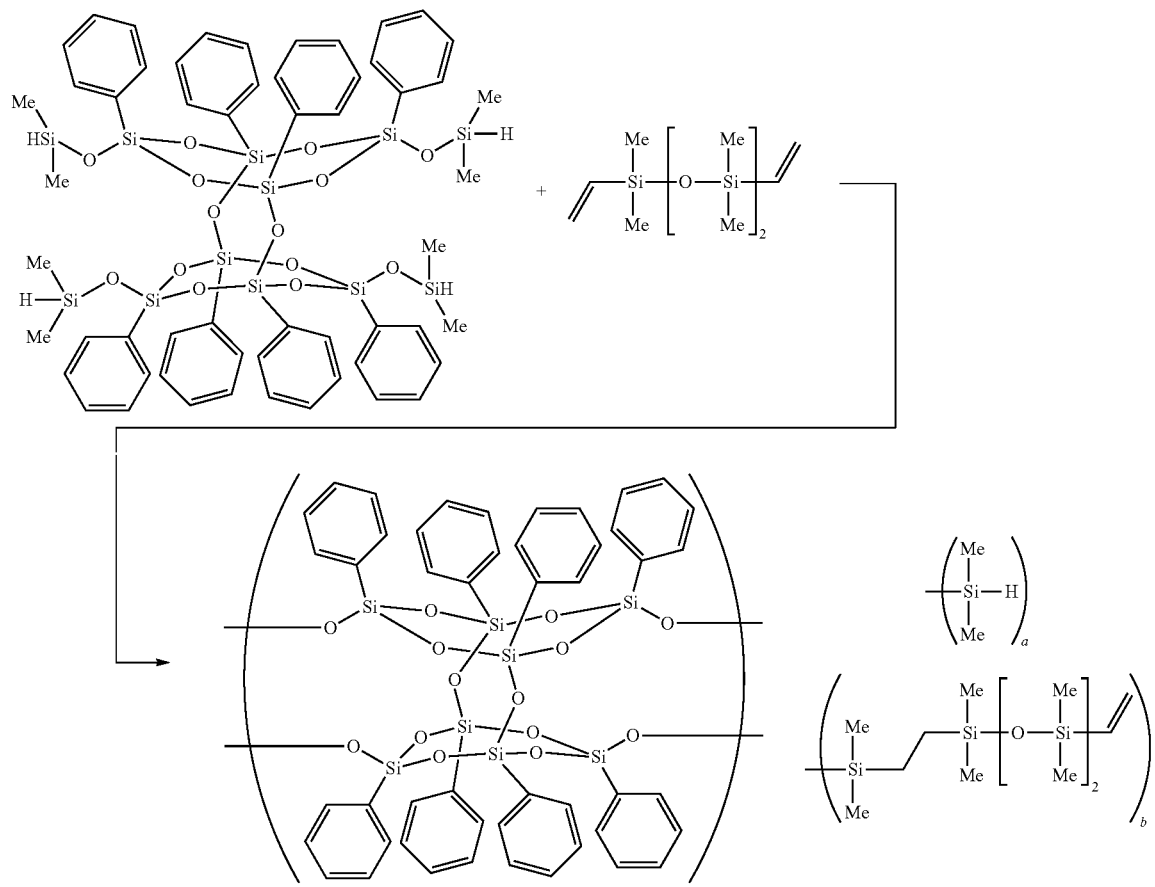

In a 200 mL (inner volume) reaction vessel equipped with a thermometer, a reflux condenser and an agitator, 50 g (0.0384 mol) of silsesquioxane derivative (DD-4H) manufactured in Synthesis Example 1, 51.3 g (0.197 mol) (5-fold In addition, a ratio of a:b was defined as described below, wherein, a=Integrated intensity of a peak of proton of SiH;
b=4−a.

Moreover, a functional group equivalent was defined as described below, wherein calculation of molecular weight: dimethyl peak in (0.0 to 0.6)/6 protons×74+double-decker unit molecular weight 1,000; wherein SiH group equivalent: molecular weight/the number of SiH (integrated intensity of a peak of proton of SiH);

vinyl group equivalent: molecular weight/the number of vinyl (integrated intensity of a peak of proton of vinyl/3 protons).

A functional group concentration was also defined in Example 2 to Example 9 as shown below, in a similar manner.

Example 2

A reaction was performed in a manner similar to Example 1 except that a change was made to 25 g (0.0192 mol) of silsesquioxane derivative (DD-4H) manufactured in Synthesis Example 1, 51.3 g (0.197 mol) (10.3-fold moles based on the mole of DD-4 H) of DVTS, 25 g of toluene as a solvent, and further to a Pt concentration of 0.016 ppm based on DD-4H. The reaction was tracked by GPC. After-treatment was carried out in a manner similar to Example 1 except that heating was stopped after 12 hours, and thus 33 g of colorless transparent liquid having a viscosity (at 25° C.) of 20 Pa·s was obtained. Analysis of molecular weight by means of GPC yielded number average molecular weight: Mn=1,381 and weight average molecular weight: Mw=1,660. The colorless transparent liquid obtained is judged to have a structure of the formula (1-1) from analytical results as described below.

$^1$H-NMR (solvent: CDCl$_3$): δ (ppm); 0.0-0.6 (m, 60.7H), 5.0 (s, 2.0H), 5.8-6.4 (m, 4.6H), 7.05-7.50 (m, 40H).

Then, a=2.0 was obtained, a SiH equivalent was 870 g/mol and a vinyl group equivalent was 1,140 g/mol.

Example 3

A reaction was performed in a manner similar to Example 1 except that a change was made to 270 g (0.207 mol) of silsesquioxane derivative (DD-4H) manufactured in Synthesis Example 1, 276 g (1.062 mol) (5.1-fold moles based on the mole of DD-4H) of DVTS and 202 g of toluene as a solvent. The reaction was tracked by GPC. Heating was stopped after 7 hours, and the resultant reaction mixture was cooled to 70° C. Then, toluene and an excess portion of DVTS were distilled off under conditions of 70° C. and a reduced pressure of 5 mmHg using a simple distillation device, and thus 325 g of colorless transparent liquid having a viscosity (at 25° C.) of 30.2 Pa·s was obtained. Analysis of molecular weight by means of GPC yielded number average molecular weight: Mn=1,400 and weight average molecular weight: Mw=1,700. The colorless transparent liquid obtained is judged to have a structure of the formula (1-1) from analytical results as described below.

$^1$H-NMR (solvent: CDCl$_3$): δ (ppm); 0.0-0.6 (m, 56.9H), 5.0 (s, 2.2H), 5.8-6.4 (m, 4.6H), 7.05-7.50 (m, 40H).

Then, a=2.2 was obtained, a SiH equivalent was 770 g/mol and a vinyl group equivalent was 1,110 g/mol.

Example 4

A reaction was performed in a manner similar to Example 1 except that a change was made to 250 g (0.192 mol) of silsesquioxane derivative (DD-4H) manufactured in Synthesis Example 1, 512.6 g (1.972 mol) (10.3-fold moles based on the mole of DD-4H) of DVTS, and 250 g of toluene, and further to a Pt concentration of 0.08 ppm based on DD-4H. The reaction was tracked by GPC. After-treatment was carried out in a manner similar to Example 1 except that heating was stopped after 12 hours, and thus 332 g of colorless transparent liquid having a viscosity (at 25° C.) of 14 Pa·s was obtained. Analysis of molecular weight by means of GPC yielded number average molecular weight: Mn=1,900 and weight average molecular weight: Mw=2,400.

The colorless transparent liquid obtained is judged to have a structure of the formula (1-1) from analytical results as described below.

$^1$H-NMR (solvent: CDCl$_3$): δ (ppm); 0.0-0.6 (m, 98.8H), 5.0 (s, 0.6H), 5.8-6.4 (m, 11.5H), 7.05-7.50 (m, 40H).

Then, a=0.6 was obtained, a SiH equivalent was 3,700 g/mol and a vinyl group equivalent was 580 g/mol.

Example 5

A reaction was performed in a manner similar to Example 1 except that a change was made to 25 g (0.0192 mol) of silsesquioxane derivative (DD-4H) manufactured in Synthesis Example 1, and 51.26 g (0.197 mol) (10.3-fold moles based on the mole of DD-4H) of DVTS, and a Karstedt catalyst at 2 ppm based on DD-4H, and further to a reaction temperature of 150° C. Disappearance of all of SiH groups was confirmed by IR, and then the reaction was terminated, an excess portion of DVTS was removed under conditions of 100° C. and 1 mmHg by means of an evaporator, and thus 35 g of colorless transparent liquid having a viscosity (at 25° C.) of 7.5 Pa·s was obtained. Analysis of molecular weight by means of GPC yielded number average molecular weight: Mn=2,200 and weight average molecular weight: Mw=2,800. The colorless transparent liquid obtained is judged to have a structure of the formula (1-1) from analytical results as described below.

$^1$H-NMR (solvent: CDCl$_3$): δ (ppm); 0.0-0.6 (m, 99H), 5.8-6.4 (m, 8.9H), 7.05-7.50 (m, 40H).

Then, a=0 was obtained, and a vinyl group equivalent was 750 g/mol.

Comparative Synthesis Example 1

A reaction was performed in a manner similar to Example 1 except that a change was made to 25 g (0.0192 mol) of silsesquioxane derivative (DD-4H) manufactured in Synthesis Example 1, 7.7 g (0.0296 mol) (1.5-fold moles based on the mole of DD-4H) of DVTS, and 19 g of toluene, and further to a Pt concentration of 0.08 ppm based on DD-4H. When the reaction was performed for 3 hours, a reaction mixture was gelated without resulting in a liquid compound.

Example 6

A reaction was performed in a manner similar to Example 1 except that a change was made to putting 50 g (0.0394 mol) of silsesquioxane derivative (DD-4H) manufactured in Synthesis Example 1, 31.1 g (0.0827 mol) (2.1-fold moles based on the mole of DD-4H) of diorganopolysiloxane 2 having vinyl groups at both ends as described in Table 1, and 18.7 g of toluene as a solvent therein, and further to a Pt concentration of 0.004 ppm based on DD-4H. The reaction was tracked by GPC. After-treatment was carried out in a manner similar to Example 1 except that heating was stopped after 6 hours, and thus 75 g of colorless transparent liquid having a viscosity (at 25° C.) of 4.2 Pa·s was obtained. Analysis of molecular weight by means of GPC yielded weight average molecular weight: Mw=2,900. In addition, non-volatile vinyl silicone that was not evaporated by distillation was left as a thermoplastic resin component as was. The colorless transparent liquid obtained is judged to have a structure as described below from analytical results as described below.

$^1$H-NMR (solvent: CDCl$_3$): δ (ppm); 0.0-0.6 (m, 81.7H), 5.0 (s, 1.9H), 5.8-6.4 (m, 5.2H), 7.05-7.50 (m, 40H).

Then, a=1.9 was obtained, a SiH equivalent was 1,060 g/mol and a vinyl group equivalent was 1,160 g/mol.

groups at both ends as described in Table 1, and 18.7 g of toluene as a solvent, and further to a Pt concentration of 0.004 ppm based on DD-4H. The reaction was tracked by GPC. The reaction was terminated by stopping heating after 3 hours, a reaction mixture was put in an evaporator, and toluene was distilled off under conditions of 70° C. and a reduced pressure of 1 mmHg by means of the evaporator. Furthermore, in order to remove a non-volatile unreacted diorganopolysiloxane, the resultant liquid was transferred to a separating funnel, 387 g of methanol was added to be sufficiently shaken, and then the resultant mixture was allowed to stand, and a lower layer was extracted. The resultant liquid was transferred to a recovery flask, and toluene was distilled off under conditions of 70° C. and a reduced pressure of 1 mmHg, and thus 20 g of colorless transparent liquid having a viscosity (at 25° C.) of 42 Pa·s was obtained. Analysis of molecular weight by means of GPC (1-2)

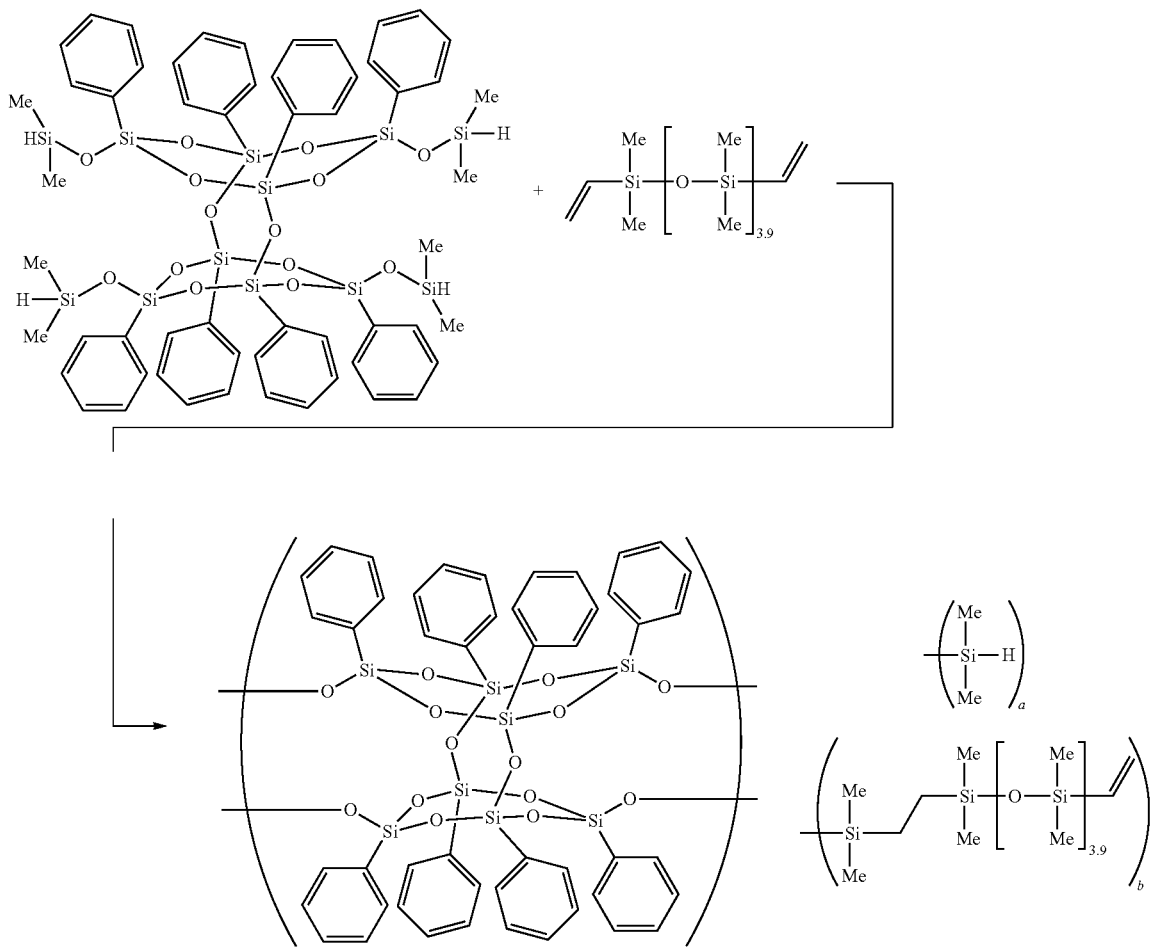

Example 7

A reaction was performed in a manner similar to Example 1 except that a change was made to 25 g (0.0197 mol) of silsesquioxane derivative (DD-4H) manufactured in Synthesis Example 1, 18.9 g (0.042 mol) (2.1-fold moles based on the mole of DD-4H) of diorganopolysiloxane 3 having vinyl yielded number average molecular weight: Mn=1,300, and weight average molecular weight: Mw=1,600. The colorless transparent liquid obtained is judged to have a structure as described below from analytical results as described below.

$^1$H-NMR (solvent: CDCl$_3$): δ (ppm); 0.0-0.6 (m, 71H), 5.0 (s, 1.8H), 5.8-6.4 (m, 2.8H), 7.05-7.50 (m, 40H).

Then, a=1.8 was obtained, a SiH equivalent was 1,040 g/mol and a vinyl group equivalent was 850 g/mol.

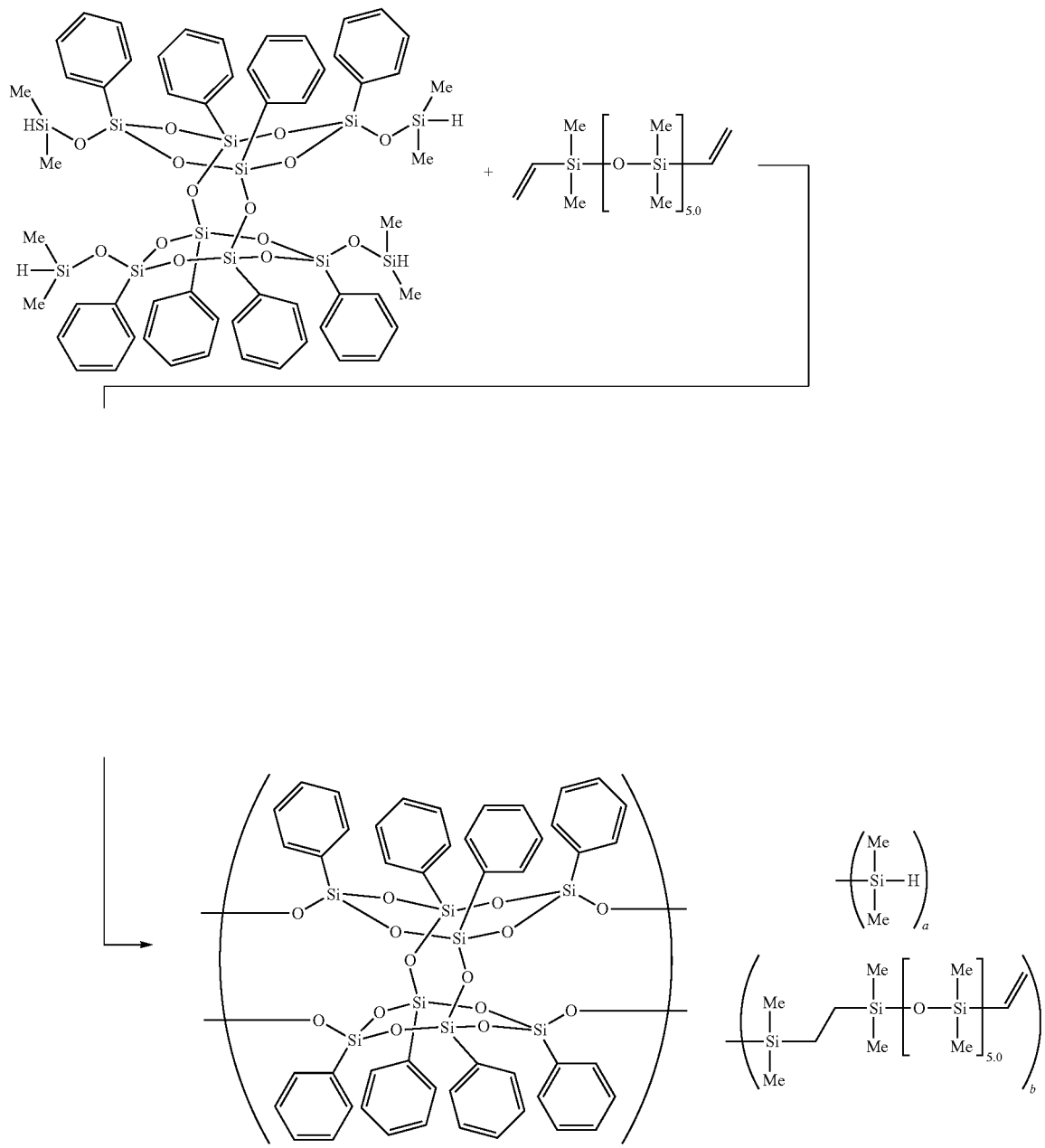

Example 8

A reaction was performed in a manner similar to Example 1 except that a change was made to putting 25 g (0.0197 mol) of double-decker silsesquioxane derivative (DD-4H) manufactured in Synthesis Example 1, 56.8 g (0.0789 mol) (4-fold moles based on the mole of DD-4H) of diorganopolysiloxane 4 having vinyl groups at both ends as described in Table 1, and 10 g of toluene as a solvent therein, and further to a Pt concentration of 1 ppm based on DD-4H. A change was made to 12 hours at a reaction temperature of 120° C. and further 6 hours at a reaction temperature of 140° C. to allow disappearance of all of SiH, and then a reaction mixture was put in an evaporator, and toluene was distilled off under conditions of 120° C. and a reduced pressure 1 mmHg by means of the evaporator, and thus 74 g of colorless transparent liquid having a viscosity (at 25° C.) of 0.6 Pa·s was obtained. Analysis of molecular weight by means of GPC yielded number average molecular weight: Mn=7,400, and weight average molecular weight: Mw=30,000. The colorless transparent liquid obtained is judged to have a structure as described below from analytical results as described below.

$^1$H-NMR (solvent: CDCl$_3$): δ (ppm); 0.0-0.6 (m, 234H), 5.0 (s, 0.0H), 5.8-6.4 (m, 10.1H), 7.05-7.50 (m, 40H).

Then, a=0 was obtained, and a vinyl group equivalent was 1,150 g/mol.

(1-4)

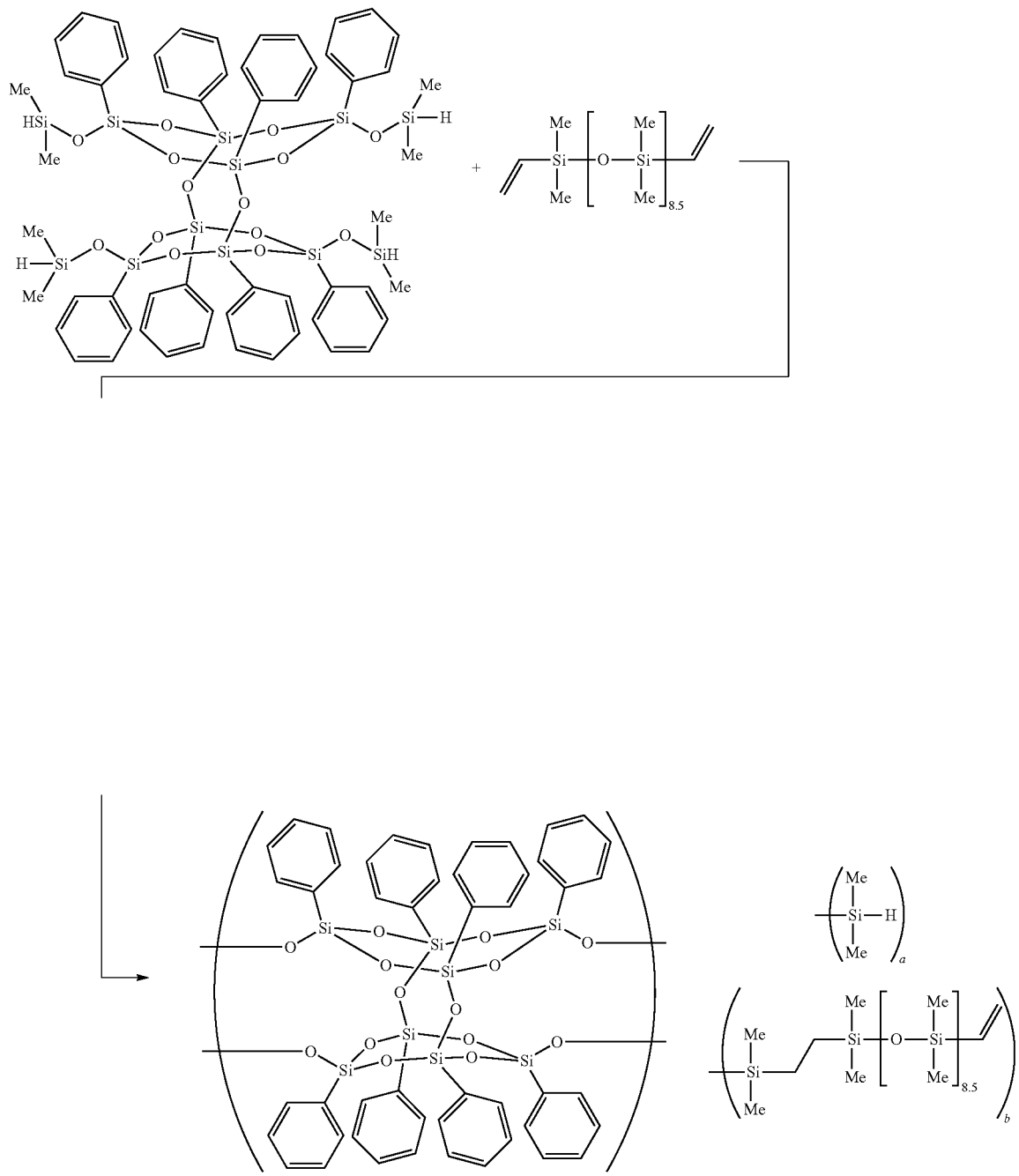

Example 9

A reaction was performed in a manner similar to Example 1 except that a change was made to 2 g (0.0015 mol) of silsesquioxane derivative (DD-4H) manufactured in Synthesis Example 1, and 25.5 g (0.0067 mol) (4.5-fold moles based on the mole of DD-4H) of diorganopolysiloxane having a phenyl group partially in a side chain, and vinyl groups at both ends (Synthesis Example 6), and further to a Pt concentration of 0.04 ppm based on DD-4H. The reaction was tracked by GPC. After-treatment was carried out in a manner similar to Example 1 except that heating was stopped after 12 hours, and thus 26 g of colorless transparent liquid having a viscosity (at 25° C.) of 0.6 Pa·s was obtained. Unreacted vinyl silicone was left as a thermoplastic resin component as was. Analysis of molecular weight by means of GPC yielded number average molecular weight: Mn=1,400 and weight average molecular weight: Mw=6,700. The colorless transparent liquid obtained is judged to have a structure as described below from analytical results as described below.

$^1$H-NMR (solvent: CDCl$_3$): δ (ppm); 0.0-0.6 (m, 116H), 4.8 (s, 0.8H), 5.4-6.4 (m, 1.8H), 7.05-7.50 (m, 70H).

Then, a=0.8 was obtained, a SiH equivalent was 18,700 g/mol and a vinyl group equivalent was 5,340 g/mol.

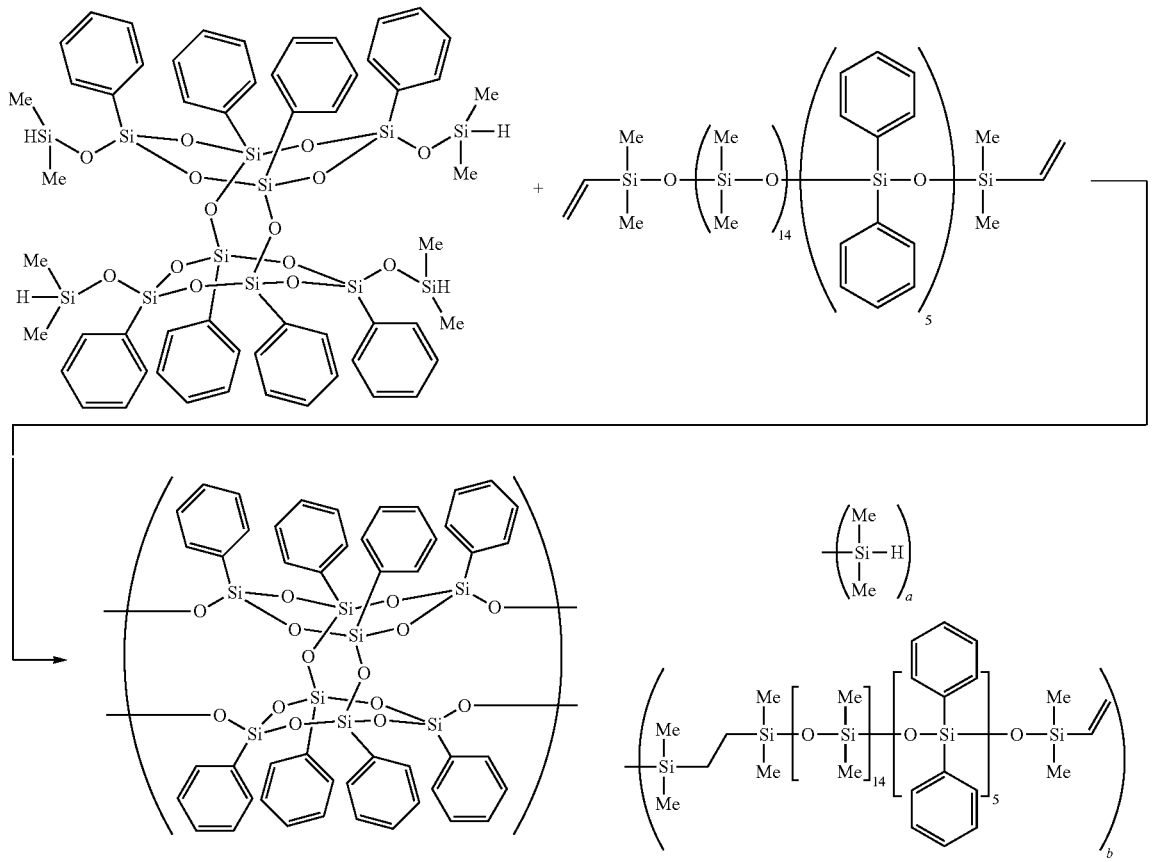

Example 10

Then, 300 g (0.230 mol) of double-decker silsesquioxane derivative (DD-4H) manufactured in Synthesis Example 1, 52.2 g (0.073 mol) (0.32-fold moles based on the mole of DD-4H) of diorganopolysiloxane 3 having vinyl groups at both ends as described in Table 1, and 304 g of toluene as a solvent were put therein to allow raw materials to dissolve by heating at 120° C. A Pt catalyst was added thereto to be a Pt concentration of 0.006 ppm based on DD-4H. The resultant reaction mixture was subjected to heating agitation at 120° C. for 16 hours to allow reaction. Herein, 256 g (0.985 mol) (4.3-fold moles based on the mole of DD-4H) of DVTS was added to further allow reaction for 6 hours. The reaction mixture was cooled to room temperature, toluene and DVTS were distilled off under conditions of 70° C. and a reduced pressure of 1 mmHg by means of an evaporator, and thus a starch syrup-like colorless transparent liquid was obtained. Analysis of molecular weight by means of GPC yielded number average molecular weight: Mn=1,400 and weight average molecular weight: Mw=3,400.

Measurement of H-NMR was carried out (in a deuterated acetone solvent) for a solution in which 1.23 g of the product obtained and 0.615 g of benzyl alcohol as an internal standard reference material were mixed. When calculated from a weight ratio and each integrated ratio of a peak at 4.6 ppm (—CH2-), a peak from 4.9 to 5.1 ppm (Si—H) and a peak from 5.6 to 6.4 ppm (—CH=CH2) among data obtained, a SiH equivalent was 770 g/mol and a vinyl equivalent was 1,600 g/mol. When calculated using the numeric values, a, b and c were a=2.37, b=1.14 and c=0.24, respectively.

Herein, the functional group equivalent was defined as described below.

SiH group equivalent: $H=(S/I)\times(M/A)\times 54$;

vinyl group equivalent: $V=(S/I)\times(M/B)\times 18$.

Wherein, each character in the formulas represents a numeric value as described below.

S: weight of a product;
I: weight of internal standard reference material;
A: peak area in 4.9 to 5.1 ppm by H-NMR;
B: peak area in 5.6 to 6.4 ppm by H-NMR;
M: peak area at 4.6 ppm by H-NMR.

In addition, a ratio of a:b:c was calculated and determined from the SiH group equivalent, the vinyl group equivalent, and a weight of charged raw materials.

$a=(V/H)\times(V+F)/(V-260)\times(1302/X)$;

$b=(X+F)/(V-260)\times(1302/X)$;

$c=(4-a-b)/2$.

Wherein, each character in the formulas represents a numeric value as described below.

H: SiH group equivalent (g/mol);
V: vinyl group equivalent (g/mol);
F: weight (g) of diorganosiloxane having vinyl groups at both ends used for synthesis;
X: weight of DD-4H used for synthesis.

(1-6)

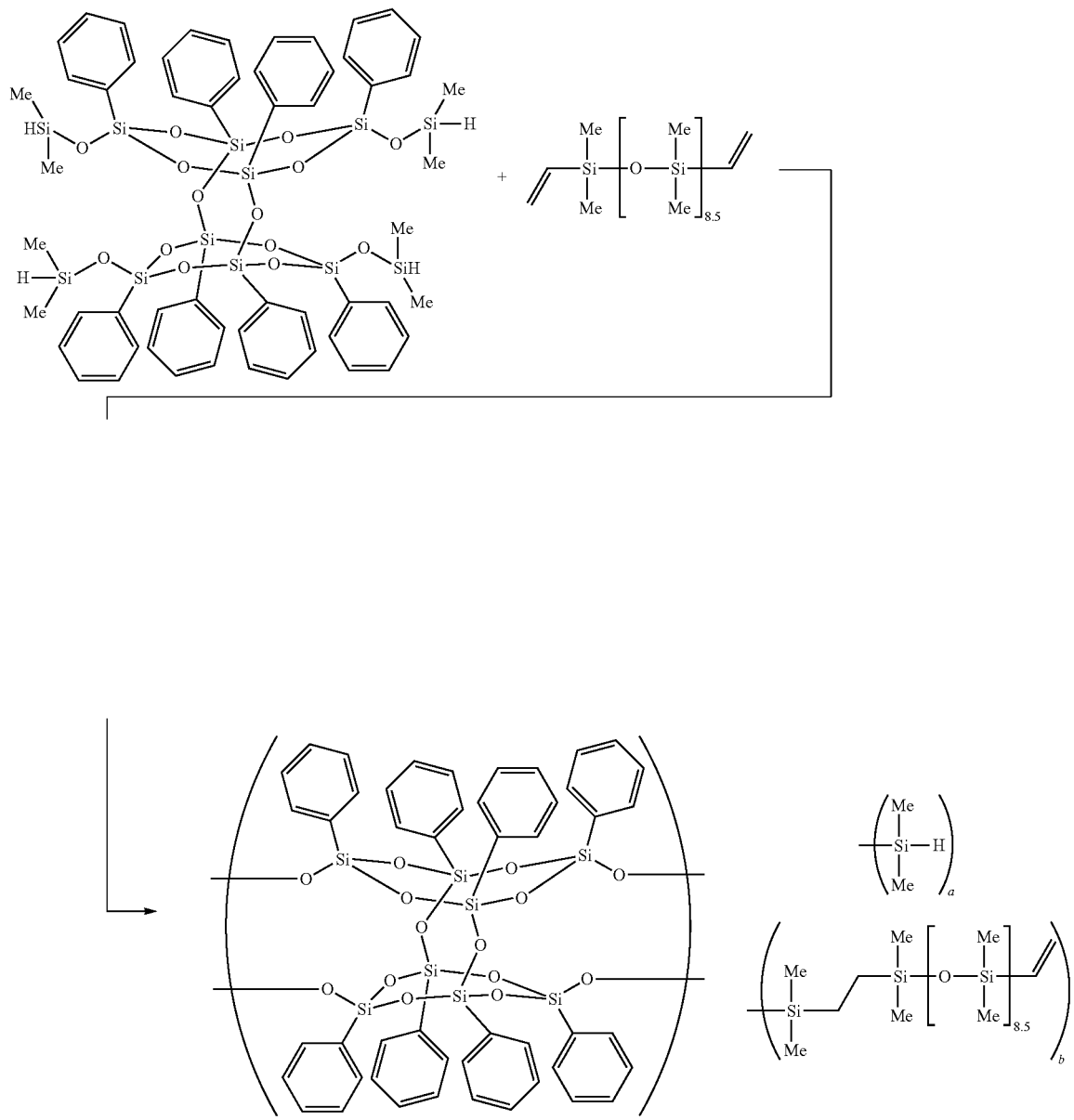

Example 11

Then, 50 g (0.0384 mol) of double-decker silsesquioxane derivative (DD-4H) manufactured in Synthesis Example 1, 18.0 g (0.02 mol) (0.52-fold moles based on the mole of DD-4H) of diorganopolysiloxane [[5]]4 having vinyl groups at both ends as described in Table 1, and 50 g of toluene as a solvent were put in a reaction vessel to allow raw materials to dissolve by heating at 120° C. A Pt catalyst was added thereto to be a Pt concentration of 0.006 ppm based on DD-4H. The resultant reaction mixture was subjected to heating agitation at 120° C. for 5 hours to allow reaction. Herein, 51.4 g (0.198 mol) (5.2-fold moles based on the mole of DD-4H) of DVTS was added to further allow reaction for 4.5 hours. The reaction mixture was cooled to room temperature, toluene and DVTS were distilled off under conditions of 70° C. and a reduced pressure of 1 mmHg by means of an evaporator, and thus a starch syrup-like colorless transparent liquid was obtained. Analysis of molecular weight by means of GPC yielded number average molecular weight: Mn=1,400 and weight average molecular weight: Mw=5,200.

Measurement of H-NMR was carried out (in a deuterated acetone solvent) for a solution in which 0.0308 g of the product obtained and 0.0184 g of benzyl alcohol as an internal standard reference material were mixed. From each integrated ratio of a peak at 4.6 ppm (—CH2- of the internal standard reference material), a peak from 4.9 to 5.1 ppm (Si—H in the polymer) and a peak from 5.6 to 6.4 ppm (—CH=CH2 in the polymer) among data obtained, a SiH equivalent was 900 g/mol and a vinyl equivalent was 2,600 g/mol. When calculated using the numeric values, a, b and c were a=2.17, b=0.74 and c=0.54, respectively.

(1-7)

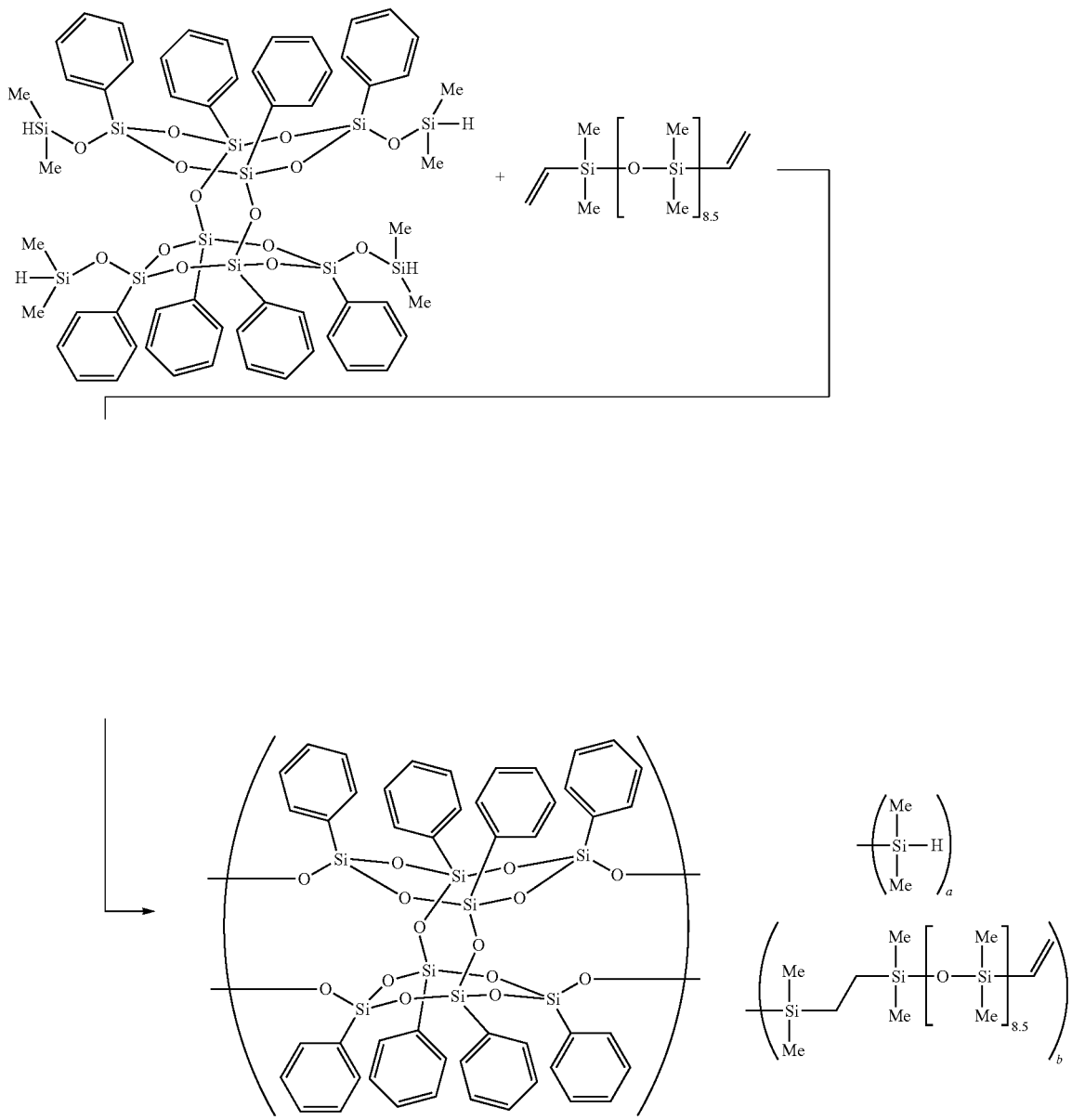

Example 12

Then, 50 g (0.0384 mol) of double-decker silsesquioxane derivative (DD-4H) manufactured in Synthesis Example 1, 13.8 g (0.0192 mol) (0.5-fold moles based on the mole of DD-4H) of diorganopolysiloxane 3 having vinyl groups at both ends as described in Table 1, and 50 g of toluene as a solvent were put in a reaction vessel to allow raw materials to dissolve by heating at 120° C. A Pt catalyst was added thereto to be a Pt concentration of 0.006 ppm based on DD-4H. The resultant reaction mixture was subjected to heating agitation at 120° C. for 4 hours to allow reaction. Herein, 51.4 g (0.198 mol) (5.2-fold moles based on the mole of DD-4H) of DVTS was added to further allow reaction for 5 hours. The reaction mixture was cooled to room temperature, toluene and DVTS were distilled off under conditions of 70° C. and a reduced pressure of 1 mmHg by means of an evaporator, and thus a starch syrup-like colorless transparent liquid was obtained. Analysis of molecular weight by means of GPC yielded number average molecular weight: Mn=1,400 and weight average molecular weight: Mw=5,100.

Measurement of H-NMR was carried out (in a deuterated acetone solvent) for a solution in which 0.0223 g of the product obtained and 0.0279 g of benzyl alcohol as an internal standard reference material were mixed. From each integrated ratio of a peak at 4.6 ppm (—CH2- of the internal standard reference material), a peak from 4.9 to 5.1 ppm (Si—H in the polymer) and a peak from 5.6 to 6.4 ppm (—CH=CH2 in the polymer) among data obtained, a SiH equivalent was 980 g/mol and a vinyl equivalent was 2,100 g/mol. When calculated using the numeric values, a, b and c were a=1.93, b=0.90 and c=0.59, respectively.

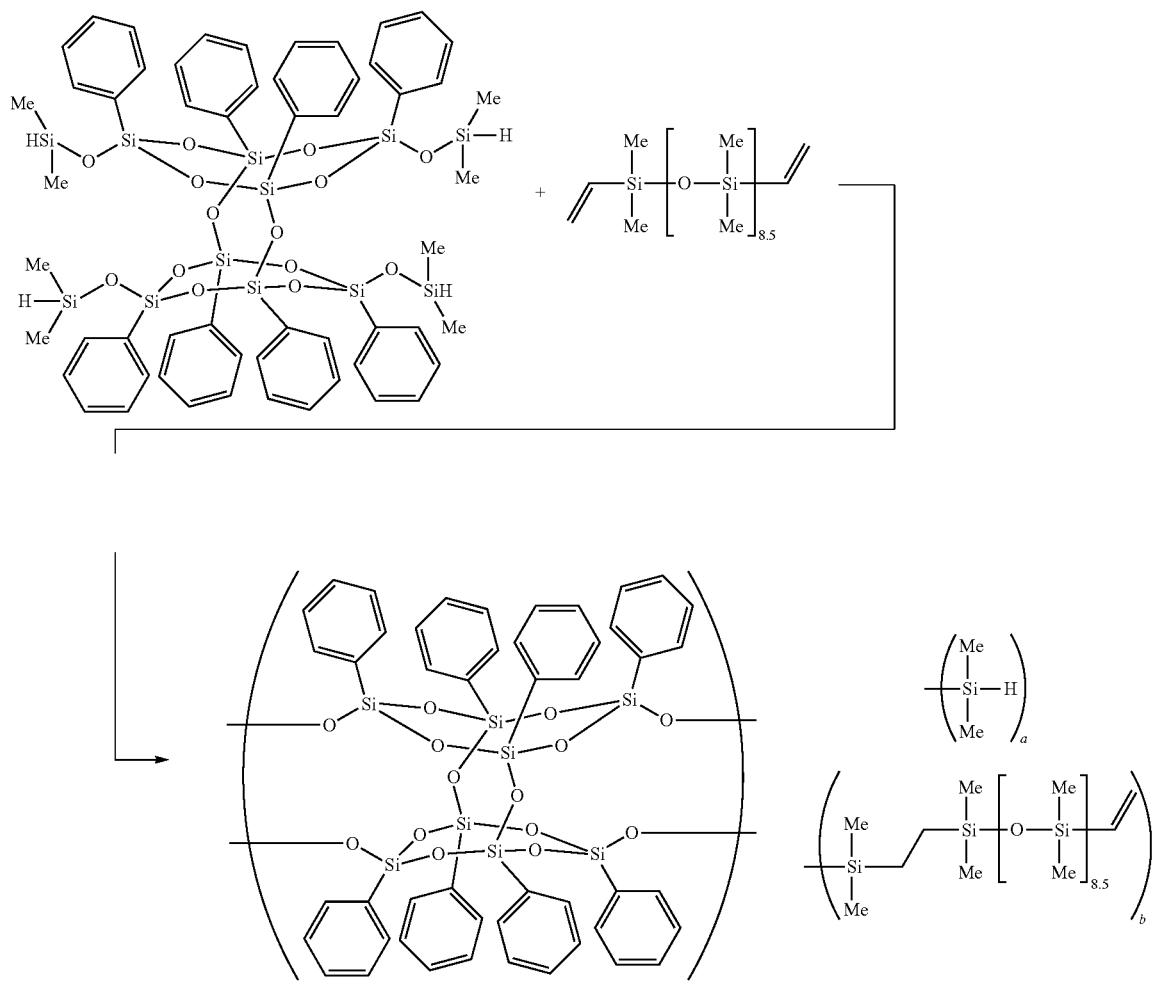

Tables 2 and 3 summarize reaction conditions, the structures obtained, the viscosity and so forth for each compound prepared in Examples 1 to 9 and Comparative Synthesis Example 1.

TABLE 2

| | n of vinyl silicone Average n | Charging conditions | | | Pt concentration ppm | Reaction temperature °C. | After-treatment conditions | Yield g | Mn | SiH equivalent g/mol | Vinyl equivalent g/mol | a | Viscosity (Pa·s) |
|---|---|---|---|---|---|---|---|---|---|---|---|---|---|
| | | Vinyl silicone g | DD-4H g | Molar ratio of vinyl silicone and DD-4H | | | | | | | | | |
| Example 1 (1-1) | 2 | 51.3 | 50 | 5 | 0.004 | 115 | 70° C. cut | 58 | 1200 | 680 | 1520 | 2.4 | 92 |
| Example 2 (1-2) | 2 | 51.3 | 25 | 10 | 0.016 | 115 | 70° C. cut | 33 | 1400 | 780 | 990 | 2 | 30 |
| Example 3 (1-3) | 2 | 276 | 270 | 5 | 0.004 | 115 | 70° C. cut | 325 | 1400 | 760 | 1100 | 2.2 | 22 |
| Example 4 (1-4) | 2 | 512.6 | 250 | 10 | 0.08 | 115 | 70° C cut | 332 | 1900 | 3500 | 580 | 0.6 | 14 |
| Example 5 (1-5) | 2 | 51.3 | 25 | 10 | 2 | 120→150 | 100° C. cut | 35 | 2200 | 0 | 740 | 0 | 7.5 |
| Comparative Synthesis Example 1 | 2 | 7.7 | 25 | 1.5 | 0.08 | 115 | — | — | Unmeasurable | Unmeasurable | Unmeasurable | Unmeasurable | Unmeasurable |

TABLE 3

|  | n of vinyl silicone Average n | Charging conditions | | | Pt concentration ppm | Reaction temperature °C. | After-treatment conditions | Yield g | Mn | SiH equivalent g/mol | Vinyl equivalent g/mol | a | Viscosity (Pa·s) |
|---|---|---|---|---|---|---|---|---|---|---|---|---|---|
|  |  | Vinyl silicone G | DD-4H (g) | Molar ratio/ DD-4H |  |  |  |  |  |  |  |  |  |
| Example 6 (1-6) | 3.9 | 31.1 | 50 | 2.1 | 0.004 | 115 | 70° C. cut | 75 | 1200 | 1040 | 1160 | 1.9 | 4.2 |
| Example 7 (1-7) | 5 | 17.2 | 25 | 2.1 | 0.004 | 115 | Methanol washing | 20 | 1300 | 1040 | 2050 | 1.8 | 42 |
| Example 8 (1-8) | 8.5 | 56.8 | 25 | 4 | 1 | 120→140 | 120° C. cut | 74 | 7400 | 0 | 1150 | 0.4 | 0.6 |
| Example 9 (1-9) | 19 | 25.5 | 2 | 4.5 | 0.04 | 115 | 70° C. cut | 26 | 1400 | 18700 | 5340 | 0.8 | 0.6 |

* In Example 9, diphenyl dimethyl vinyl silicone was used as a raw material.

Comparative Synthesis Example 2

Then, 4 g of silsesquioxane derivative (DD-4H) manufactured in Synthesis Example 1, 2.3 g of 1,3-divinyltetramethyldisiloxane (made by Gelest, Inc.), and 0.1 g of platinum catalyst (3 wt. % xylene solution of platinum(0)-1,3-divinyl-1,1,3,3-tetramethyldisiloxane catalyst, made by Aldrich Corporation) were dissolved in 20 mL of tetrahydrofuran (dehydrated, made by Kanto Chemical) to allow reaction at 60° C. for 3 hours under nitrogen, and thus a silsesquioxane polymer was prepared. When number average molecular weight of the polymer was measured by a GPC method, the number average molecular weight was 1,700, and inferior to 10,000. Moreover, the polymer colored yellow, and was not suitable as a thermosetting resin for a LED-use encapsulant in which transparency is required.

Comparative Hardened Material Example 1

Moreover, 1.64 g of silsesquioxane polymer obtained in Comparative Synthesis Example 2 and 1 g of divinyltetramethyldisiloxane were mixed, and made as thermosetting resin composition 14. Table 4 shows a compounding amount (g) of thermosetting resin composition 14. Thermosetting resin composition 14 was poured into a glass mold, and then heated at 100° C. for 30 minutes, and subsequently heated at 200° C. for 3 hours, but was not hardened at all.

<Preparation of a Thermosetting Resin Composition>

In a screw vial, a mixture of a compound prepared in the Examples, and DVTS or polyorganosiloxane prepared in the Synthesis Examples were put. The screw vial was set to a Planetary Centrifugal Mixer ("Thinky Mixer (registered tradename)" ARE-250, made by Thinky Corporation), and the resultant mixture was mixed and defoamed. A silane coupling agent: S510 (3-glycidoxypropyltrimethoxysilane, made by Chisso Corporation) was added to be 0.025% by weight in a concentration thereof, a hardening retarder: MVS-H (1,3,5,7-tetravinyl-1,3,5,7-tetramethylcyclotetrasiloxane, made by Chisso Corporation) was added to be 10 ppm in a concentration thereof, and a platinum catalyst was added to be 1 ppm in a concentration thereof, and the resultant mixture was again mixed and defoamed by means of the Planetary Centrifugal Mixer, and thus thermosetting resin compositions 1 to 12 were obtained. Table 4 shows a compounding amount (g) of each thermosetting resin composition.

Moreover, as a comparative hardening composition, DD-4H in which a is 4, and DVTS were mixed, and the resultant mixture was made as thermosetting resin composition 13. Table 4 shows a compounding amount (g) of thermosetting resin composition 13. As shown in Table 5, when DD-4H in which a is 4 was used for the thermosetting resin composition, a homogeneous solution was not formed after mixing and defoaming the mixture to cause phase separation, and a hardened material was not obtained even by heating the mixture.

TABLE 4

|  | Thermosetting resin composition | | | | | | | | | | | | | | | |
|---|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 | 15 | 16 |
| Compound prepared in Example 1 | 10 | 5 |  |  |  |  |  |  |  |  | 4 |  |  |  |  |  |
| Compound prepared in Example 2 |  |  | 10 | 10 |  |  |  |  |  |  |  |  |  |  |  |  |
| Compound prepared in Example 3 |  |  |  |  | 7 | 10 | 5 |  |  |  |  |  |  |  |  |  |
| Compound prepared in Example 4 |  |  |  |  |  |  |  | 2 |  |  |  |  |  |  |  |  |

TABLE 4-continued

| | Thermosetting resin composition | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Compound prepared in Example 5 | | | | | | | 0.71 | | 4 | | | | | | | |
| Compound prepared in Example 6 | | | | | | | | | | 10 | 10 | | | | | |
| Compound prepared in Example 7 | | | | | | | | | | | | | | | | |
| Compound prepared in Example 8 | | | | | | | | | | | | 2 | | | | |
| DD-4H | | | | | | | | | | | | | | 5 | | |
| Compound prepared in Synthesis Example 7 | | | | | | | | 9 | 5 | | | | | | | |
| Compound prepared in Example 10 | | | | | | | | | | | | | 10 | | | |
| Compound prepared in Example 11 | | | | | | | | | | | | | | | 5 | |
| Compound prepared in Example 12 | | | | | | | | | | | | | | | | 5 |
| DVTS | 0.8 | | 0.35 | | | 0.12 | | | 1.2 | | | | 0.46 | | 0.47 | 0.35 |
| Compound prepared in Synthesis Example 4 | | 0.71 | | 0.98 | | 1.1 | | | | | 0.4 | | | 1.8 | | |
| Compound prepared in Synthesis Example 5 | | | | | | | 0.54 | | | | | | | | | |

Table 5 shows viscosity of the thermosetting resin composition obtained by compounding the thermosetting resin composition as shown in Table 4, and mixing the compositions, and a refractive index and hardness of a hardened material obtained by hardening the composition.

Table 5 shows that, as for the viscosity of the thermosetting resin composition of the invention, a composition having a wide viscosity range can be provided from an optimum viscosity range from 1 Pa·s to 10 Pa·s that is suitable for a dispenser system used for LED encapsulation to an optimum

TABLE 5

| | Hardened material | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 14 | 15 | 16 | 13 |
| Thermosetting resin composition | 1 | 2 | 3 | 4 | 5 | 6 | 7 | 8 | 9 | 10 | 11 | 12 | 14 | 15 | 16 | 13 |
| Viscosity | 2.1 | 2.5 | 9.5 | 6.2 | 30 | 2.8 | 7.3 | 5.5 | 35 | 4.2 | 2.1 | 4.5 | 3.6 | 5.7 | 6.0 | Unmeasurable due to phase separation |
| Refractive index | 1.52 | 1.51 | 1.51 | 1.51 | 1.52 | 1.51 | 1.51 | 1.5 | 1.5 | 1.5 | 1.5 | 1.51 | 1.5 | 1.5 | 1.51 | Unmeasurable due to no hardened material obtained |
| Hardness | D70 | D60 | D70 | D65 | D70 | D65 | D50 | D30 | D40 | D40 | D30 | D30 | D30 | D30 | D30 | Unmeasurable due to no hardened material obtained | viscosity range of 10 Pa·s or more that is suitable for a mold system. Moreover, use of the thermosetting resin composition of the invention allows provision of the hardened material having a high refractive index of 1.5 or more.

<Preparation of a Hardened Material>

As for the thermosetting resin composition, two glass plates were set by inserting a Naflon SP packing made by NICHIAS Corporation (diameter: 4 mm) therebetween as a spacer. The thermosetting resin composition was poured into a space thereof, and was subjected to defoaming under reduced pressure. Then, the thermosetting resin composition was heated at 80° C. for 1 hour, and subsequently 150° C. for 1 hour in the above order to allow hardening thereof, the two glass plates were pealed, and thus a 4 mm-thick hardened material having a smooth surface was obtained.

<Measurement of Luminous Transmittance>

A transmittance at 400 nm was measured by means of UV-Vis Spectrophotometer UV-1650 made by Shimadzu Corporation.

<Refractive Index>

As a test specimen, a hardened material was cut by means of a band saw machine, and the test specimen was prepared according to JIS K7142. A refractive index was measured using the test specimen and using the D line (586 nm) of a sodium vapor lamp by means of Abbe refractometer (NAR-2T, made by ATAGO Co., Ltd.). As an intermediate liquid, methylene iodide was used.

<Hardness>

According to JIS K6253, hardness was measured by means of durometer WR-105D made by Nishitokyo Seimitsu Co., Ltd.

<Heat-Resistance Test>

A heat-resistance test was carried out according to a method as described below and heat resistance was evaluated. Two pieces of 4 mm-thick hardened materials were prepared, a luminous transmittance of each hardened material was measured by means of UV-Vis Spectrophotometer, and made as an initial transmittance. The hardened material was put in an oven (constant temperature dryer: DX302, made by Yamato Scientific Co., Ltd.) at 180° C., and subjected to heat treatment for a fixed period of time (1,000 hours in Table 6).

<Heat-Resistant Transparency>

A luminous transmittance of a hardened material after testing was measured by means of UV-Vis Spectrophotometer, and from a transmittance at 400 nm, a retention rate at the wavelength ((transmittance after heat treatment for a fixed period of time/initial transmittance at each wavelength) 100) was calculated, and heat-resistant transparency was evaluated. A retention rate of luminous transmittance at 180° C. is preferably 90% or more.

<Adhesion Strength Test for a Polyphthalamide Resin>

A test was carried out according to JIS K6850. As a test specimen, a thermosetting resin composition was placed between sheets prepared by adjusting a dimension of a polyphthalamide resin (Amodel (trade name) A-4122NLWH905, made by Solvay Advanced Polymers, LLC), as a base material, according to JIS K6850, and the test specimen was prepared by heating the composition at 80° C. for 1 hour, and then at 150° C. for 1 hour and hardening the composition. As an adhesion test, adhesion strength was measured using a load cell of 5 kN by means of a tensile compression testing machine (Autograph AGS-500B, made by Shimadzu Corporation).

<Adhesion Strength Test for Ag>

A test was carried out according to JIS K6850. As a test specimen, a thermosetting resin composition was placed between silver-plated standard test substrates (made by Nihon Testopanel Co., Ltd.), as a base material, and the test specimen was prepared by heating the composition at 80° C. for 1 hour, and then at 150° C. for 1 hour for hardening the composition. As an adhesion test, adhesion strength was measured using a load cell of 5 kN by means of a tensile compression testing machine (Autograph AGS-500B, made by Shimadzu Corporation).

<Heat Cycle Test>

A heat cycle test was carried out by putting the adhesion test specimen prepared according to the method in a test area of cold & hot impact tester TSE-11 made by ESPEC Corporation, and 100 cycles were repeated, in which one cycle includes exposure at −40° C. for 30 minutes and exposure at 105° C. for 30 minutes. In addition, the test was carried out at a shift time of 2 minutes between both exposure temperatures.

After the heat cycle, an adhesion test was carried out by means of the tensile compression testing machine, and a close contact ratio retention rate was evaluated in terms of a reduction ratio of adhesion strength after the heat cycle relative to the initial adhesion strength measured as described above.

<High Pressure and High Humidity Test>

A thermosetting resin composition was injected by means of a dispenser into a power LED-use premolded package having a thickness of 1.5 mm, a side of 5 mm, an opening having a diameter of 3.5 mm, and a silver-plated bottom to allow heating of the composition at 80° C. for 1 hour and then at 150° C. for 1 hour and hardening the composition. The hardened material was put in an electric pressure cooker made by Matsushita Electric Industrial Co., Ltd., and boiled for 59 minutes under a pressurized condition of 98 kPa. Then, a housing as described above was put in pure water containing red ink, and boiled for 1 hour. Close contact was evaluated depending on presence or absence of penetration of the red ink. If no penetration of the red ink was observed, the close contact was favorable, and the hardened material was rated to be good, and if any penetration of the red ink was observed, the close contact was poor, and the hardened material was rated to be bad.

Tables 2 and Table 3 show that the liquid organosilicon compound of the invention has viscosity in the range of 100 Pa·s or less at room temperature. Therefore, the thermosetting resin composition containing the liquid organosilicon compound allows wide provision of a product from an optimum viscosity range from 1 Pa·s to 10 Pa·s that is suitable for the dispenser system in encapsulating an optical semiconductor, to an optimum viscosity range of 10 Pa·s or more that is suitable for the mold system.

Table 6 shows the results of evaluation of heat resistance of the test specimen obtained from hardened material 5, hardened material 6, hardened material 9, hardened material 10, hardened material 11 and a hardened material (Comparative 2) obtained by hardening a commercially available two-liquid type silicone for encapsulating a light emitting diode.

TABLE 6

| Hardened material | | 5 | 6 | 8 | 9 | 10 | 11 | 14 | Comparative 2 |
|---|---|---|---|---|---|---|---|---|---|
| Thermosetting resin composition | | 5 | 6 | 8 | 9 | 10 | 11 | 14 | Comparative 2 |
| Transmittance (%) at 400 nm | | 98 | 98 | 98 | 98 | 98 | 98 | 97 | 97 |
| Refractive index | | 1.52 | 1.51 | 1.50 | 1.50 | 1.50 | 1.50 | 1.50 | 1.53 |
| Heat-resistant test at 180° C. for 1,000 hours | Yellowing | No | No | No | No | No | No | No | Yes |
| | Retention rate (%) of transmittance at 400 nm | 94 | 94 | 91 | 94 | 94 | 94 | 96 | 79 |
| | Hardness change | D70 → D70 | D65 → D65 | D30 → D30 | D40 → D42 | D30 → D30 | D30 → D30 | D24 → D28 | D40 → D60 |

Table 6 shows that the hardened material obtained using the thermosetting resin composition of the invention had characteristics of both a high transparency and a high refractive index, and was excellent in resistance to thermal yellowing, as compared with a phenyl silicone encapsulation resin that has been applied so far. Furthermore, Table 6 shows that, while the phenyl silicone encapsulation resin that has been applied so far had a problem of generating cracks due to a rise of hardness when exposed to heat for a long period of time, the hardened material obtained using the thermosetting resin composition of the invention had no change in hardness and was excellent in crack resistance, even if exposed to heat for a long period of time.

Table 7 shows the results of evaluation of close contact of the test specimen obtained from hardened material 1, hardened material 4, hardened material 6, hardened material 7 and a hardened material (Comparative 2) obtained by hardening a commercially available two-liquid type silicone for encapsulating a light emitting diode.

TABLE 7

| Hardened material | 1 | 4 | 6 | 7 | Comparative 2 |
|---|---|---|---|---|---|
| Thermosetting resin composition | 1 | 4 | 6 | 7 | Commercially available two-liquid type silicone for encapsulating a light emitting diode |
| Close contact with PPA | 4 | 3.8 | 3.4 | 3.8 | 1.7 |
| Close contact with Ag | 4.2 | 3.4 | 5.5 | 3.2 | 2.6 |

Table 7 shows that the hardened material obtained using the thermosetting resin composition of the invention is excellent in close contact, as compared with the phenyl silicone encapsulation resin that has been applied so far.

Table 8 shows the results of evaluation of close contact ratio retention rate after the heat cycle test for the test specimen obtained using hardened material 5, and the hardened material (Comparative 2) obtained by hardening the commercially available two-liquid type silicone for encapsulating the light emitting diode.

TABLE 8

| Hardened material | 5 | Comparative 2 |
|---|---|---|
| Thermosetting resin composition | 5 | Commercially available two-liquid type silicone for encapsulating a light emitting diode |
| PPA close contact force retention rate | 87% | 42% |

Table 8 shows that the hardened material obtained using the thermosetting resin composition of the invention had a smaller decrease in close contact due to a heat shock, and was superior in long-term reliability as an LED-use encapsulant, as compared with the phenyl silicone encapsulation resin that has been applied so far.

Table 9 shows the results of evaluation of boiling test at a high temperature and a high pressure for hardened material 5, and the hardened material (Comparative 2) obtained by hardening the commercially available two-liquid type silicone for encapsulating the light emitting diode in the power LED-use premolded package having a thickness of 1.5 mm, a side of 5 mm, an opening having a diameter of 3.5 mm, and a silver-plated bottom.

TABLE 9

| Hardened material | 5 | Comparative 2 |
|---|---|---|
| Thermosetting resin composition | 5 | Commercially available two-liquid type silicone for encapsulating a light emitting diode |
| Close contact | Good | Bad |

Table 9 shows that the hardened material obtained using the thermosetting resin composition of the invention had, even under conditions of a high temperature and a high humidity, no penetration of the red ink and maintains close contact with the LED housing, and is excellent in long-term reliability as the LED-use encapsulant.

Thus, the hardened material obtained using the thermosetting resin composition of the invention has been found to have characteristics of both a high transparency and a high refractive index, to be excellent in resistance to thermal yellowing, adhesion strength and stress relaxation capability, as compared with the phenyl silicone encapsulation resin that has been applied so far. Moreover, the hardened material of the invention has a skeleton of a double decker silsesquioxane, and is found to be excellent in insulating properties.

INDUSTRIAL APPLICABILITY

A hardened material of the invention can be utilized for an optical semiconductor encapsulation material, an insulating film, a sealing agent, an adhesive, an optical lens or the like.

What is claimed is:

1. A method for manufacturing a liquid organosilicon compound represented by formula (1) as described below:

(1)

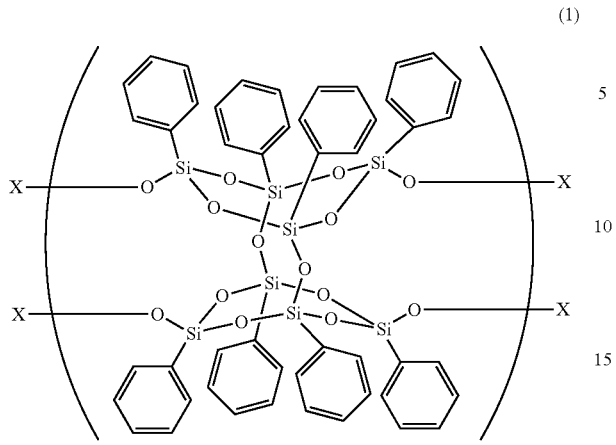

wherein, X is each independently a group represented by formula (I), formula (II) or formula (III) as described below, and when the number of the group represented by formula (I) per one molecule of the liquid organosilicon compound represented by general formula (I) (or the mean number of groups per one molecule of the compound when the compound is a mixture having a different ratio for the group represented by formula (I), the group represented by formula (II), and the group represented by formula (3), is defined as a, the number of the group represented by formula (II) per one molecule thereof is defined as b, and the number of the group represented by formula (III) per one molecule thereof is defined as c, $0 \leq a \leq 3.5$, $0 \leq b \leq 3.5$, and $0 \leq c \leq 1$ are obtained, and also $a+b+2c=4$ is obtained:

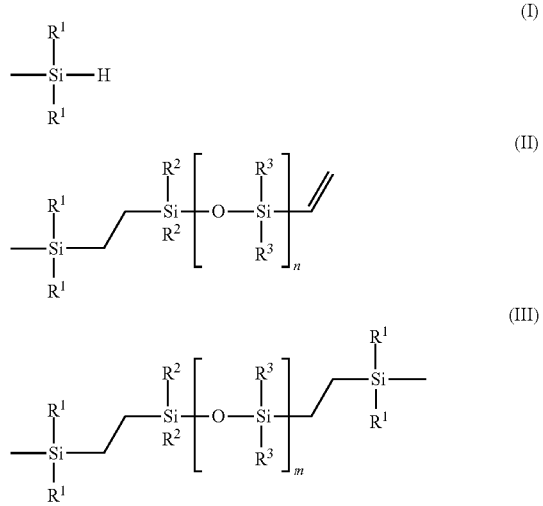

wherein, $R^1$ is each independently a group selected from alkyl having 1 to 4 carbons, cyclopentyl and cyclohexyl, $R^2$ and $R^3$ are each independently a group selected from alkyl having 1 to 4 carbons, cyclopentyl, cyclohexyl and phenyl, m and n are the number of repetitions of —OSi$(R^3)_2$—, and a mean value satisfying 1 to 50, the method comprising a process for allowing a hydrosilylation reaction between a compound represented by general formula (2-1) as described below and a compound represented by general formula (2-2) as described below while a Pt catalyst is added, wherein the hydrosilylation reaction and liquefaction is allowed in an amount of twice or more the number of moles of the general formula (2-2) based on the number of the moles of the general formula (2-1), and an amount of Pt catalyst is in a concentration range of 0.001 to 0.08 ppm based on the compound represented by formula (2-1):

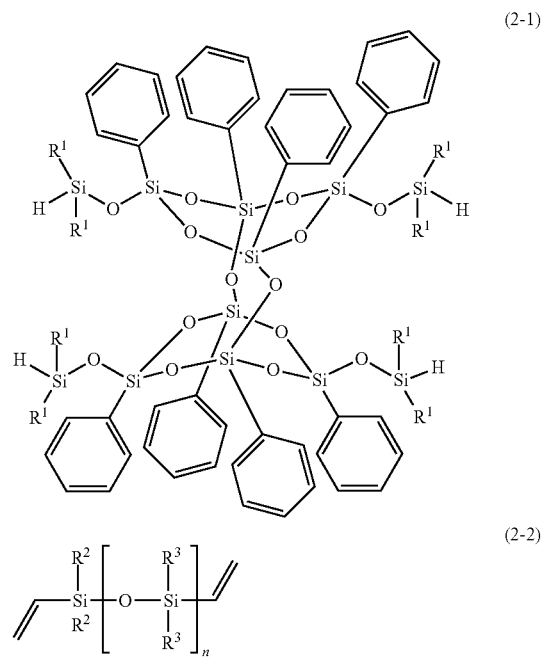

wherein, in the general formulas (2-1) and (2-2), $R^1$, $R^2$, $R^3$ and n are defined in a manner similar to the definitions in general formula (1).

2. A thermosetting resin composition containing a liquid organosilicon compound manufactured by the method according to claim 1.

3. The thermosetting resin composition according to claim 2, further containing a liquid organosilicon compound obtained from a constitutional unit represented by C, and a constitutional unit represented by D in formula (3):

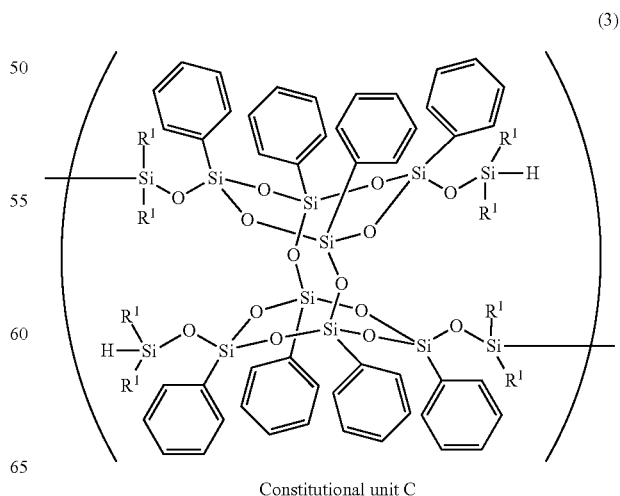

Constitutional unit C

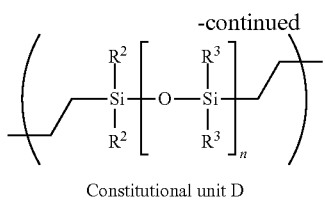

Constitutional unit D wherein, in the formula (3), $R^1$ is each independently a group selected from alkyl having 1 to 4 carbons, cyclopentyl and cyclohexyl, $R^2$ and $R^3$ are each independently a group selected from alkyl having 1 to 4 carbons, cyclopentyl, cyclohexyl and phenyl, n is the number of repetitions of —$OSi(R^3)_2$—, and a mean value satisfying 2 to 50, and when a molar fraction of the constitutional unit represented by C in the liquid organosilicon compound is defined as α, and a molar fraction of the constitutional unit represented by D in the liquid organosilicon compound is defined as β, a ratio of α to (n×β), (α:(n×β)), satisfies 1:3 to 1:100.

4. The thermosetting resin composition according to claim 2, further containing a platinum catalyst.

5. The thermosetting resin composition according to claim 2, further allowing dispersion of silica and/or a phosphor.

6. A hardened material, formed by thermally hardening the thermosetting resin composition according to claim 2.

7. A molded object obtained by molding the hardened material according to claim 6.

8. A coating film, formed by applying the thermosetting resin composition according to claim 2.

9. An encapsulation material for an optical semiconductor, composed of the thermosetting resin composition according to claim 2.

* * * * *